(12) United States Patent
Sun et al.

(10) Patent No.: US 9,359,366 B2
(45) Date of Patent: Jun. 7, 2016

(54) INTERMEDIATE OF TICAGRELOR AND PREPARATION METHOD THEREFOR, AND PREPARATION METHOD FOR TICAGRELOR

(71) Applicants: Jiangsu Hengrui Medicine Co., Ltd., Lianyungang, Jiangsu (CN); Suncadia Pharmaceuticals Co., Ltd., Chengdu, Sichuan (CN)

(72) Inventors: Shaoguang Sun, Sichuan (CN); Defu Song, Sichuan (CN); Biao He, Sichuan (CN); Xiaobo Lai, Sichuan (CN)

(73) Assignees: Jiangsu Hengrui Medicine Co., Ltd., Lianyungang, Jiangsu (CN); Suncadia Pharmaceuticals Co., Ltd., Chengdu, Sichuan (CN)

(*) Notice: Subject to any disclaimer, the term of this patent is extended or adjusted under 35 U.S.C. 154(b) by 0 days.

(21) Appl. No.: 14/781,803

(22) PCT Filed: Mar. 13, 2014

(86) PCT No.: PCT/CN2014/073388
§ 371 (c)(1),
(2) Date: Oct. 1, 2015

(87) PCT Pub. No.: WO2014/166324
PCT Pub. Date: Oct. 16, 2014

(65) Prior Publication Data
US 2016/0052928 A1 Feb. 25, 2016

(30) Foreign Application Priority Data

Apr. 10, 2013 (CN) .......................... 2013 1 0122613
Aug. 28, 2013 (CN) .......................... 2013 1 0383474

(51) Int. Cl.
| C07D 487/04 | (2006.01) |
| C07D 405/12 | (2006.01) |
| C07D 239/48 | (2006.01) |
| C07D 239/47 | (2006.01) |

(52) U.S. Cl.
CPC ............ *C07D 487/04* (2013.01); *C07D 239/47* (2013.01); *C07D 239/48* (2013.01); *C07D 405/12* (2013.01)

(58) Field of Classification Search
CPC .................................................. C07D 487/04
See application file for complete search history.

(56) References Cited

U.S. PATENT DOCUMENTS

| 6,525,060 | B1 | 2/2003 | Hardern et al. | |
| 8,273,879 | B2* | 9/2012 | Larsson | C07D 239/47 544/301 |
| 8,563,755 | B2* | 10/2013 | Bohlin | C07D 317/44 549/437 |
| 8,802,850 | B2* | 8/2014 | Rao | A61K 31/519 424/133.1 |
| 9,233,966 | B2* | 1/2016 | Dahanukar | C07C 253/30 |
| 2003/0148888 | A1 | 8/2003 | Larsson et al. | |
| 2007/0293513 | A1* | 12/2007 | Bohlin | C07D 487/04 514/261.1 |
| 2013/0317220 | A1* | 11/2013 | Nair | C07C 271/24 544/254 |
| 2014/0256747 | A1* | 9/2014 | Zupancic | C07D 239/56 514/261.1 |
| 2014/0371449 | A1* | 12/2014 | Maras | C07C 271/24 544/254 |

FOREIGN PATENT DOCUMENTS

| CN | 102149716 A | 8/2011 |
| CN | 102659815 A | 9/2012 |
| CN | 102675321 A | 9/2012 |
| CN | 102875537 A | 1/2013 |
| WO | 0192263 A1 | 12/2001 |
| WO | 2010030224 A1 | 3/2010 |
| WO | 2011017108 A2 | 2/2011 |

(Continued)

OTHER PUBLICATIONS

PCT/CN2014/073388, International Preliminary Report on Patentability (Oct. 13, 2015).*

(Continued)

*Primary Examiner* — Alexander R Pagano
(74) *Attorney, Agent, or Firm* — Panitch Schwarze Belisario & Nadel LLP

(57) ABSTRACT

Disclosed are intermediates of Ticagrelor and a preparation method therefor, and a preparation method for Ticagrelor. Specifically, disclosed is an intermediate, namely, a compound of Formula (VI), for preparing Ticagrelor. Further disclosed is a method for preparing the intermediate and a method for preparing Ticagrelor by using the intermediate. Ticagrelor is prepared by using the intermediate, so that the synthesis process is simple, and a defect that long reaction times under high temperature that are required in the existing methods are avoided. The method is suitable for mass production in industry, energy consumption is reduced, pollution of the environment is reduced, and discharge of waste is reduced.

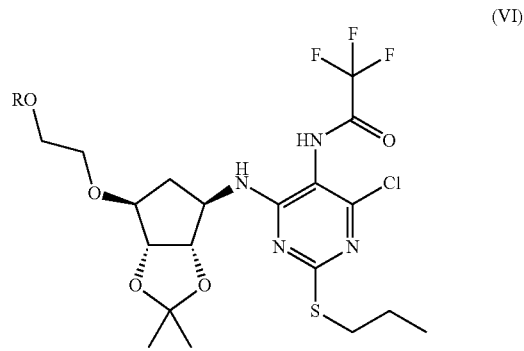

(VI)

24 Claims, No Drawings

(56) References Cited

FOREIGN PATENT DOCUMENTS

| WO | 2012085665 | A2 | | 6/2012 | | |
|----|------------|----|---|--------|---|---|
| WO | 2012138981 | A2 | | 10/2012 | | |
| WO | WO 2012138981 | A2 | * | 10/2012 | ........... | C07D 487/04 |

OTHER PUBLICATIONS

T Greene, Protection for the Amino Group in, Greene'S Protective Groups in Organic Synthesis (4th ed., 2007).*
International Search Report issued Jun. 17, 2014 in International Application No. PCT/CN2014/073388.

* cited by examiner

INTERMEDIATE OF TICAGRELOR AND PREPARATION METHOD THEREFOR, AND PREPARATION METHOD FOR TICAGRELOR

CROSS-REFERENCE TO RELATED APPLICATION

This application is a Section 371 of International Application No. PCT/CN2014/073388, filed Mar. 13, 2014, which was published in the Chinese language on Oct. 16, 2014 under International Publication No. WO 2014/166324 A1, and the disclosure of which is incorporated herein by reference in its entirety.

FIELD OF THE INVENTION

The present disclosure relates to novel synthesis methods for Ticagrelor, a selective anticoagulant and key intermediate thereof, and belongs to the technical field of pharmaceutical manufacturing.

BACKGROUND OF THE INVENTION

Ticagrelor, a trade name, with the chemical name being (1S,2S,3R,5S)-3-(3-(((1R,2S)-2-(3,4-difluorophenyl)cyclopropyl)-5-(propylthio)-3H-[1,2,3]triazolo[4,5-d]pyrimidin-7-ylamino)-5-(2-hydroxyethoxy)cyclopentane-1,2-diol, is a chemical having the structural formula as shown in Formula (I) below:

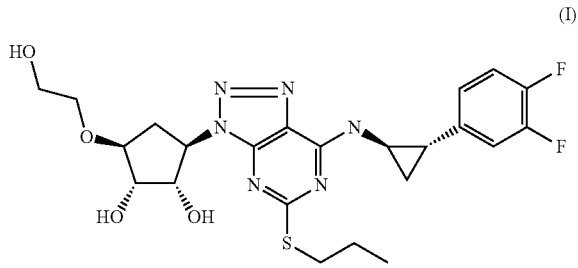

(I)

The chemical is a cyclopentyl-triazolo-pyrimidine, a novel and selective anticoagulant developed by AstraZeneca (UK), and the first reversibly binding adenosine diphosphate (ADP) antagonist targeting the P2Y12 receptor. This chemical is able to reversibly act on the purinoceptor 2 subtype P2Y12 on the vascular smooth muscle cell (VSMC). This chemical has a significant inhibitory effect on platelet aggregation caused by ADP, and is able to improve the acute coronary disease symptoms effectively. Since this chemical's antiplatelet effect is reversible, it is particularly applicable to those patients who need anticoagulant therapy prior to surgery. Compared with Clopidogrel, a competitor, Ticagrelor is superior in terms of clearly reducing symptoms of myocardial infarction, stroke or cardiovascular death, and is thus an anticoagulant with a promising future.

In the prior art, the patent literatures related to Ticagrelor synthesis methods include U.S. Pat. No. 6,525,060, US20030148888, WO2011017108, CN102659815A, CN102675321A, CN102149716A, WO2012085665, WO2012138981, WO2012138981, etc. These existing patents/patent applications have disclosed many synthesis methods and processes for preparing Ticagrelor.

Chinese patent application No. CN102149716A (AstraZeneca, the original research company) discloses a synthesis route for preparing Ticagrelor (I), comprising the steps of using 2-[[(3aR,4S,6R,6aS)-6-aminotetrahydro-2,2-dimethyl-4H-cyclopenta[d]-1,3-dioxolalkenyl-4-yl]oxy]ethanol of Formula (I-1) and 4,6-dichloro-2-propylthiopyrimidine-5-amine as the starting materials to get a key intermediate (I-2); ring closing of the intermediate (I-2) in the presence of an appropriate alkali metal nitrite to get an intermediate (I-3); reacting the intermediate (I-3) with an appropriate salt of (1R,2S)-REL-2-(3,4-difluorophenyl)cyclopropylamine; and finally removing the protecting group.

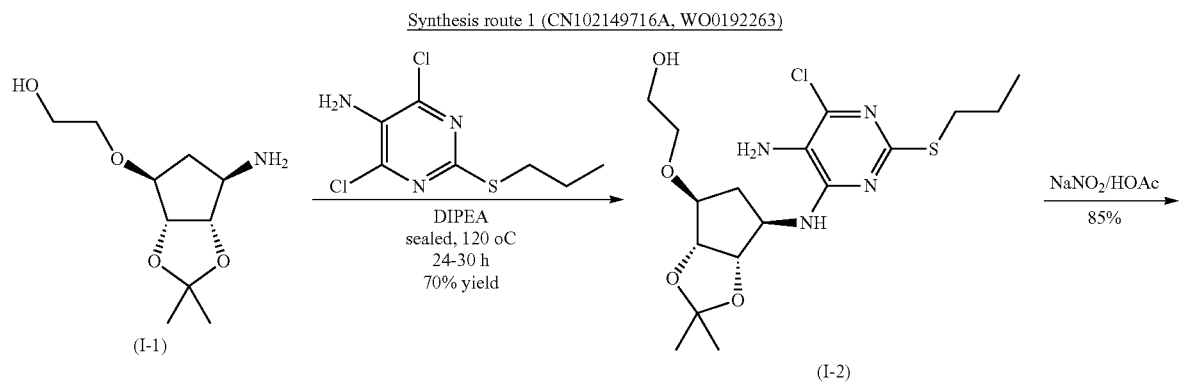

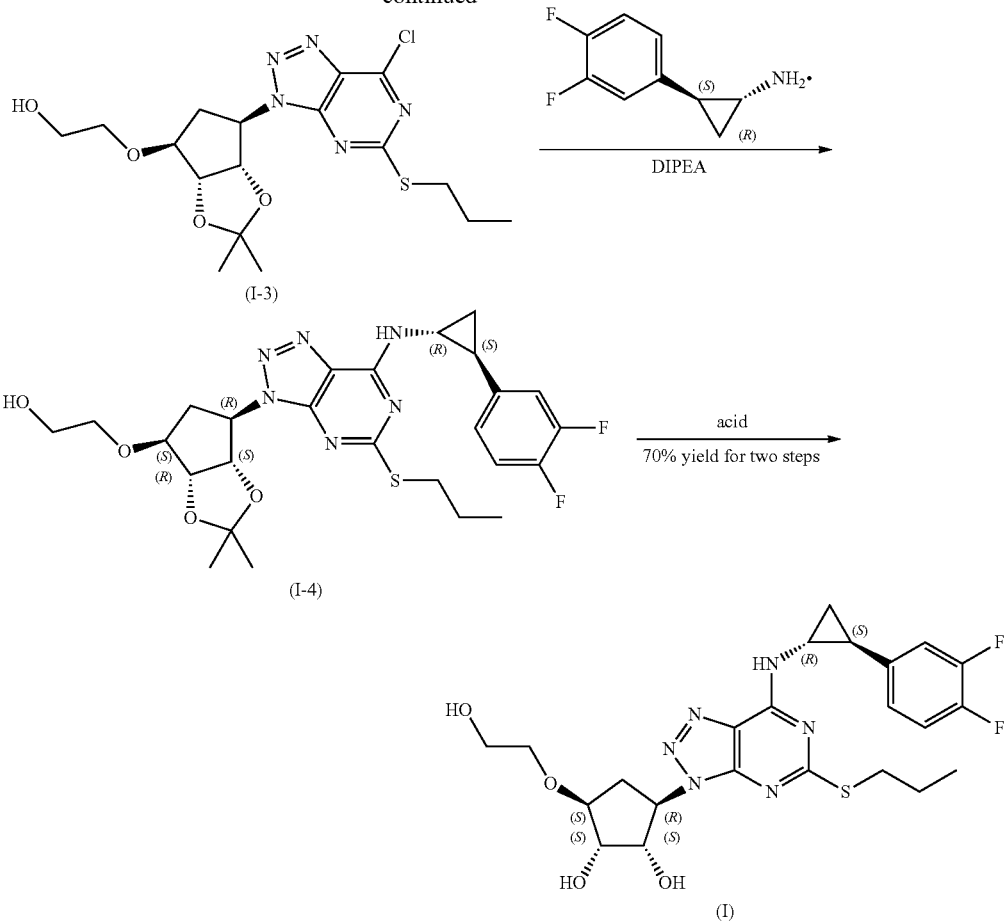

Based on published information, the route of synthesis described in patent applications CN102149716A and WO0192263 is the existing industrial production process developed by the original research company to prepare bulk pharmaceutical chemicals of Ticagrelor. The synthesis of the key intermediate (I-2) is the key control point of the process. The reaction requires a high temperature, as well as an oxygen-free environment and a certain pressure condition for a long time. Thus, the reaction is limited due to certain equipment. Since the reaction is carried out under high temperature and pressure conditions for a long time, there is also a potential danger in terms of industrial production.

Chinese patent application No. CN102675321A discloses a synthesis route for preparing Ticagrelor (I), comprising the steps of using 2-[[(3aR,4S,6R,6aS)-6-aminotetrahydro-2,2-dimethyl-4H-cyclopenta[d]-1,3-dioxolalkenyl-4-yl]oxy] ethanol (II-1) protected by an alkoxy or a silyl reagent and 4,6-dichloro-2-propylthiopyrimidine-5-amine as the starting materials to prepare a key intermediate (II-2); ring closing of the intermediate (II-2) in the presence of an appropriate alkali metal nitrite to prepare an intermediate (II-3); reacting the intermediate (II-3) with an appropriate salt of (1R,2S)-REL-2-(3,4-difluorophenyl)cyclopropylamine; and finally removing the protecting group.

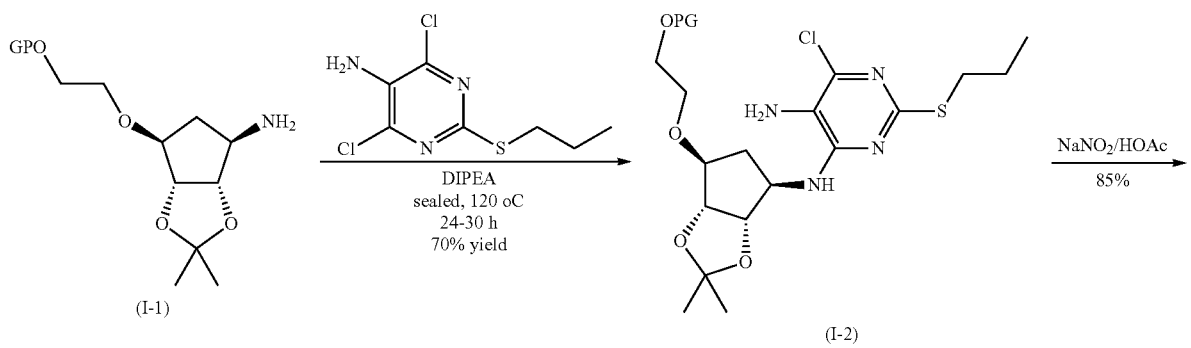

-continued

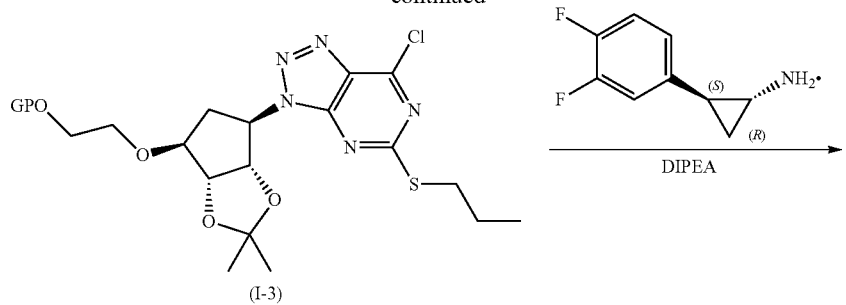

(I-3)

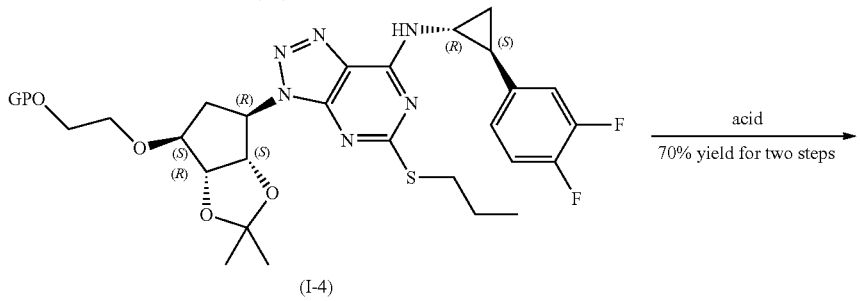

(I-4)

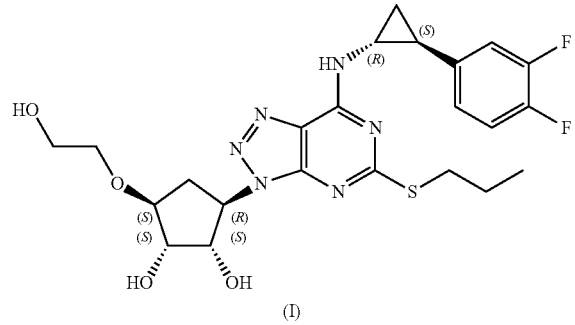

(I)

This method has the same characteristics as those of the original research company's patent application No. CN102149716A and WO0192263 in terms of the synthesis strategy. The defects of the method lie in that the reaction still requires a high temperature, as well as an oxygen-free environment and a certain pressure condition for a long time; the resulting intermediate is of low purity and dark color, making it troublesome to purify the final product and difficult to remove the color; and the total yield of the process is quite low.

U.S. Pat. No. 6,525,060 discloses a synthesis route for preparing Ticagrelor (I), comprising the steps of reacting 4,6-dichloro-5-nitro-2-(propylthio)pyrimidine with (3aR,4S,6R,6aS)-6-aminotetrahydro-2,2-dimethyl-4H-cyclopenta[d]-1,3-dioxolalkenyl-4-ol (III-1) to get an intermediate (III-2); reducing the intermediate (III-2) in an iron powder/acetic acid system; ring closing of the resulting product in the presence of a nitrite; and finally carrying out a series of reactions, including ammoniation, bromination and a substitution reaction.

Synthesis route 3 (US6525060)

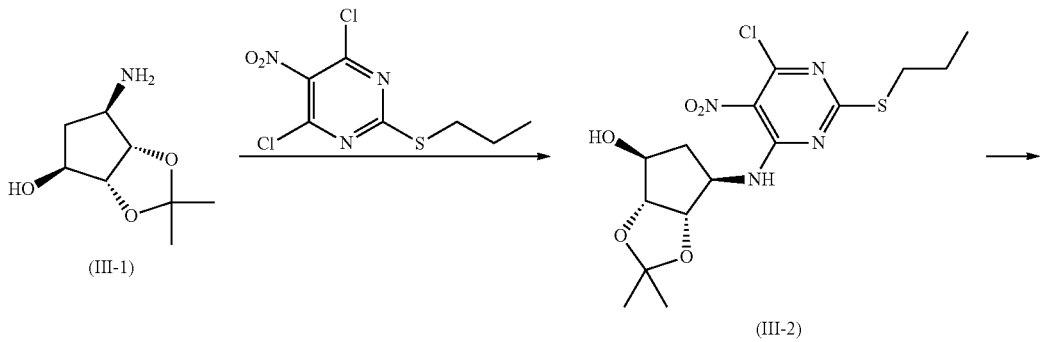

-continued
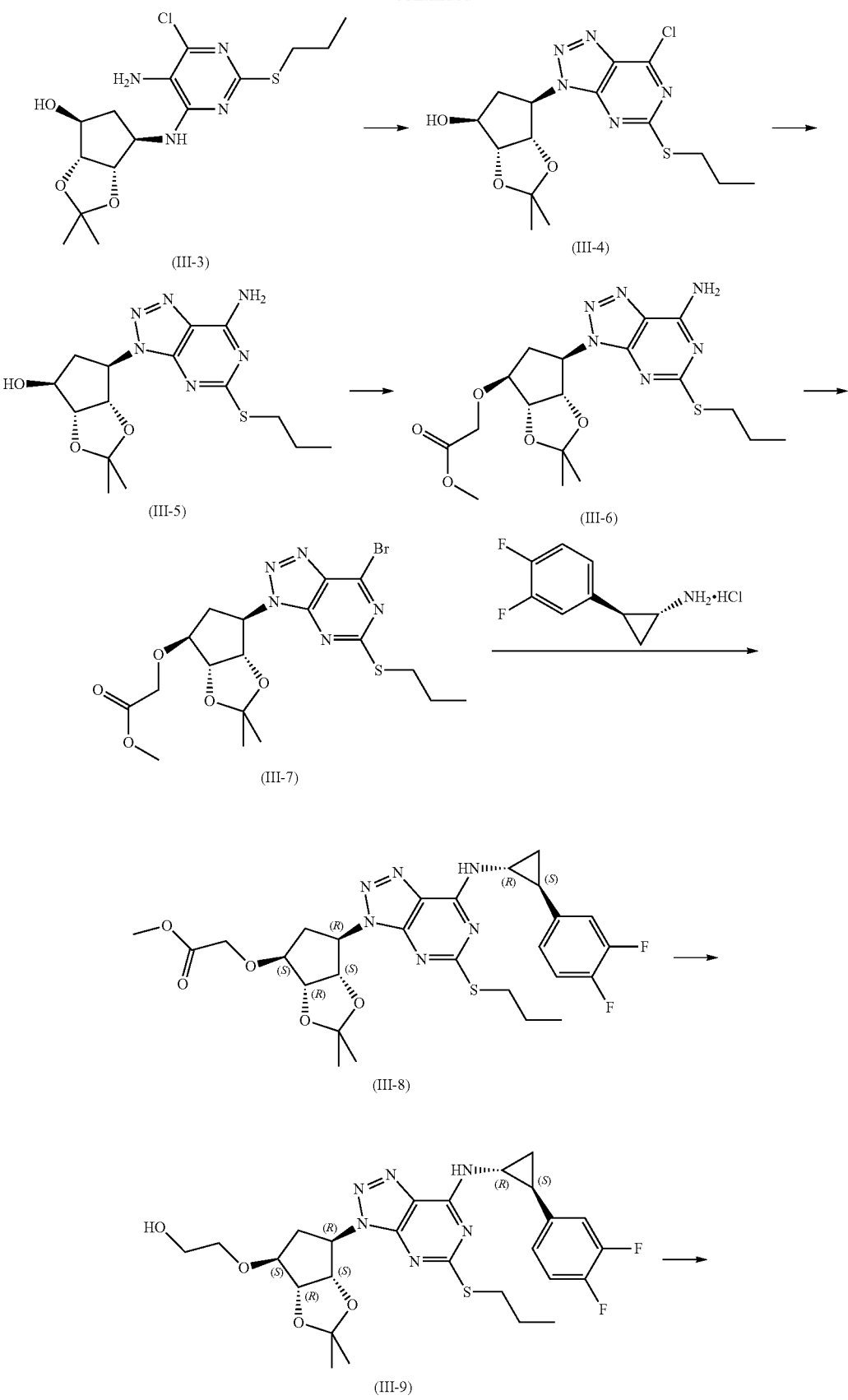

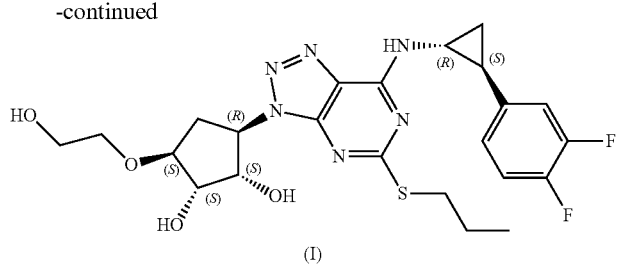

(I)

The method has a prolonged route, wherein due to the strong electron-withdrawing effect of the nitro group, the chlorines on positions 4 and 6 of 4,6-dichloro-5-nitro-2-(propylthio)pyrimidine are of high activity, and readily react with the amino group and the hydroxyl group of the molecule of (III-1). The reaction system is typically complicated, and the resulting intermediate is difficult to purify. The entire route involves many reactions under harsh conditions, such as bromination, ammoniation and the application of butyl lithium reagent. In view of all of these, together with other disadvantages, it is clear that this route is not suitable for industrial production.

Patent application No. CN102875537A discloses a synthesis route for preparing Ticagrelor of Formula (I), comprising the steps of reacting 4,6-dichloro-5-nitro-2-(propylthio)pyrimidine with a protected amino alcohol of Formula (IV-2) to get an intermediate of Formula (IV-3); reducing the nitro group of the intermediate (IV-3) under the catalyst of palladium-carbon to get an intermediate of Formula (IV-4); ring closing of the intermediate (IV-4) in the presence of a nitrite to get an intermediate of Formula (IV-5); reacting the intermediate (IV-5) with a chiral cyclopropylamine to get an intermediate of Formula (IV-6); reducing the intermediate (IV-6) with sodium borohydride under the catalyst of sodium bromide to get an intermediate of Formula (IV-7); and finally removing the propylidene protecting group under an acidic condition.

Synthesis route 4 (CN102875537A)

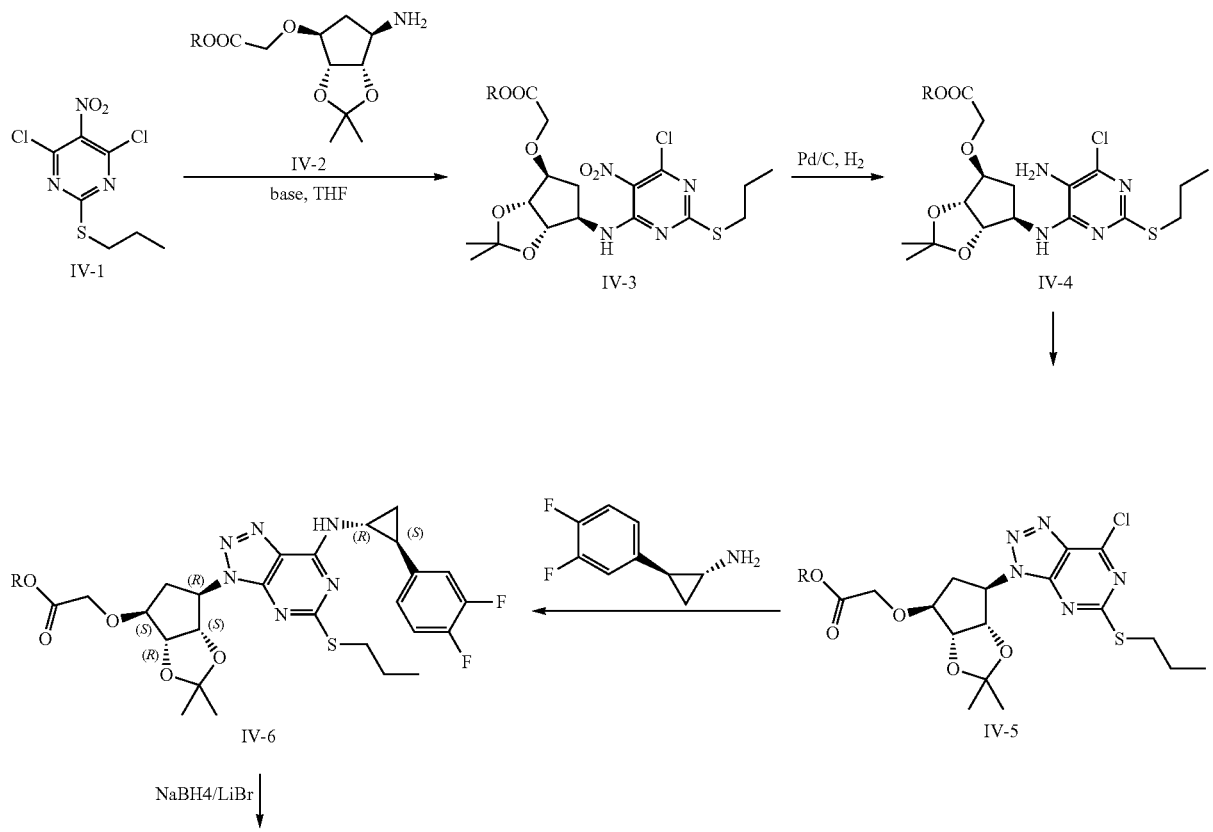

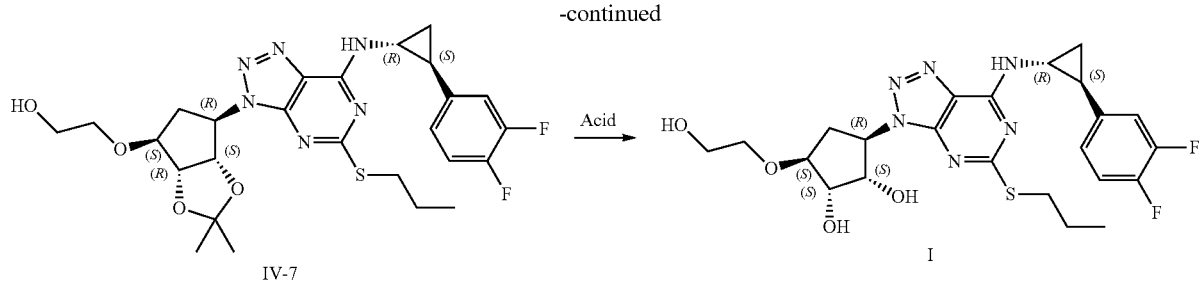

This route has similar problems as those of U.S. Pat. No. 6,525,060. It is difficult to control the selectivity of the reaction in the first step. In addition, the intermediate of Formula (IV-2), an amino-acid ester, is naturally of poor stability due to severe intermolecular amino-ester exchange reaction, resulting in less industrial feasibility. Moreover, during the hydrogenation of the intermediate of Formula (IV-3) under the catalyst of palladium-carbon, the chlorine atom on the pyrimidine ring tends to be removed by hydrogenation, and the resulting contaminant is difficult to remove completely, but finally brought to the product, resulting in high difficult purification of the product, low yield and high cost. Accordingly, this route is not suitable for industrial production.

International Patent Application No. WO2012138981 discloses a synthesis route for preparing Ticagrelor of Formula (I), comprising the steps of starting from 4,6-dichloro-5-nitro-2-(propylthio)pyrimidine by a classic aromatic amine protection method to get 4,6-dichloro-2-(propylthio)-5-formamidopyrimidine (V-1); reacting (V-1) with a chiral amino acid of Formula (V-2) in the presence of an appropriate base to get an intermediate of Formula (V-3); removing the formyl group and the hydroxyl protecting group on the side chain of the intermediate (V-3) under an appropriate acidic condition to get an intermediate of Formula (V-4); reacting the intermediate (V-4) with an alkali metal nitrite to get an intermediate of Formula (V-5); reacting the intermediate (V-5) with a chiral cyclopropylamine to prepare an intermediate of Formula (V-6); and finally reducing the intermediate (V-6) with sodium borohydride.

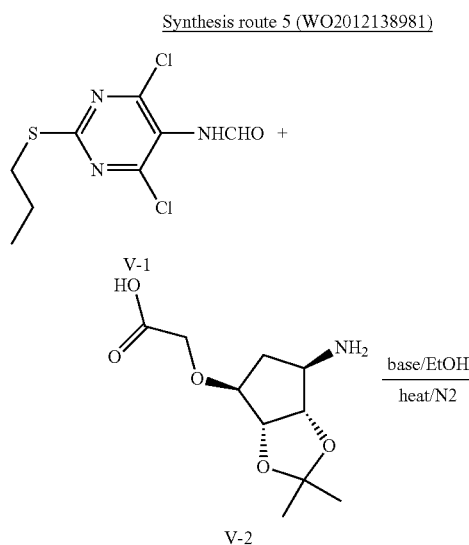

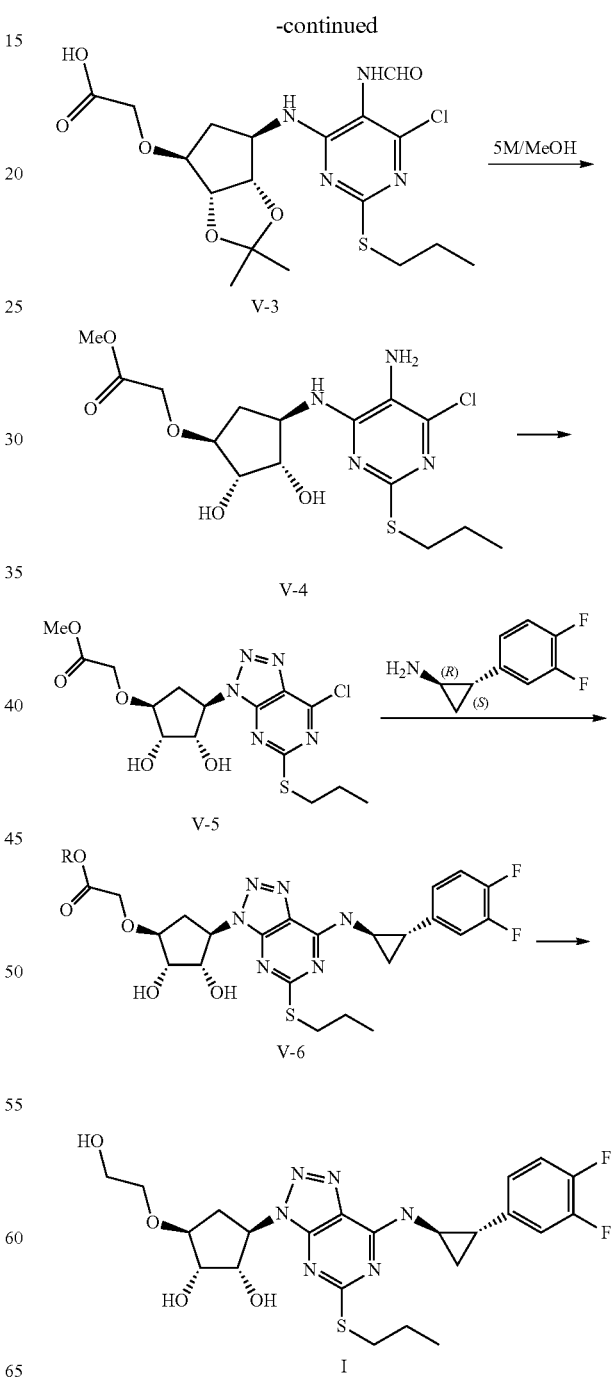

This route has an advantage of conciseness. The adoption of formyl group protection is able to activate the chlorine atom in the molecule of aminopyrimidine, thereby making a mild condition for the substitution reaction. However, the adoption of an acidic system to remove the formyl group in the subsequent process makes it inevitable to remove the propylidene protecting group on the side chain, resulting in great polarity of the subsequent intermediates, which is unfavorable to the purification of the intermediates. Moreover, the presence of several exposed hydroxyl groups reduces the stability of the intermediate (V-5), such that intermolecular autoreaction is easy to carry out, thereby making it difficult to purify the final product.

BRIEF SUMMARY OF THE INVENTION

On the basis of the analysis on the prior art of Ticagrelor synthesis, it is found that the electronic effect of the substituent group at position 5 of the pyrimidine ring as the mother nucleus has a great influence on the leaving capability of the ortho halogen atom. When there is a nitro group with strong electron-withdrawing capability at position 5, the ortho halogen atom is readily substituted by a nucleophilic reagent, resulting in harsh reaction conditions (such as low-temperature, oxygen-free and anhydrous conditions), usually various byproducts, and the difficult purification of the intermediates. On the contrary, when there is a free amino group at position 5, the strong electron donating effect of the amino group allows the leaving capability of the halogen atom on the pyrimidine ring to be reduced, resulting in the need of intensive conditions, such as high-temperature, high-pressure and long-time reaction to carry out the substitution reaction.

Accordingly, it is necessary to select an appropriate amino protecting group to activate the leaving capability of the ortho halogen atom, thereby achieving mild conditions for the substitution reaction and easy purification of intermediates. By carefully screening amino protecting groups, it is found that when a trifluoroacetylation reagent is adopted to protect the amino group on the pyrimidine ring, not only is the reaction for introducing trifluoroacetyl group carried out under a mild condition (for example, when trifluoroacetic anhydride is adopted as the protecting reagent, it is able to get the protected intermediate quantitatively within 1 hour at room temperature), but also after trifluoroacetyl group is adopted to protect the amino group, the leaving capability of the ortho halogen atom is activated effectively, enabling the substitution reaction to be carried out under mild conditions, for example, reaction temperature ranging from 30° C. to 80° C., reaction time of 1 h to 5 h, no need of inert atmosphere protection for the reaction system and so on. Additionally, the inventors have also tried the method as mentioned in International Patent Application No. WO2012138981, wherein a formyl group is applied to protect the amino group. The experimental results showed that the reaction for selectively introducing the formyl group at the amino group on the pyrimidine ring must be carried out in the presence of greatly excessive anhydrous formic acid and acetic anhydride as the solvent system, the reaction time was long, and the resulting intermediate with the protected amino group was usually mixed with acetyl protected byproduct, resulting in difficult purification of the intermediate and typically around 70% yield.

In one aspect, the present disclosure provides a compound of Formula (VI):

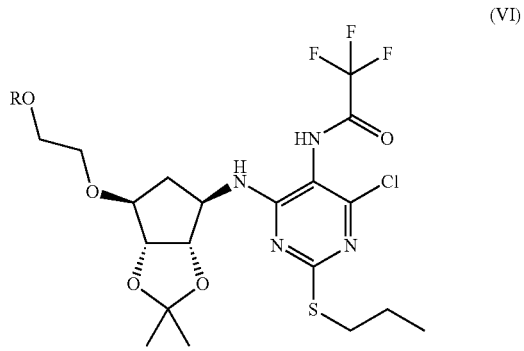

wherein R is hydrogen or a hydroxyl protecting group; and said hydroxyl protecting group is preferably selected from the group consisting of triethylsilyl, triisopropylsilyl, t-butyldimethylsilyl, t-butyldiphenylsilyl, methoxymethyl, tetrahydropyranyl and tetrahydrofuranyl.

The compound of Formula (VI) can be easily used to prepare Ticagrelor.

In another aspect, the present disclosure provides a preparation method for the compound of Formula (VI), comprising a step of reacting a compound of Formula (VIII) with a compound of Formula (VII) or a salt thereof:

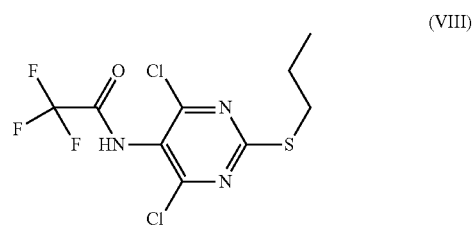

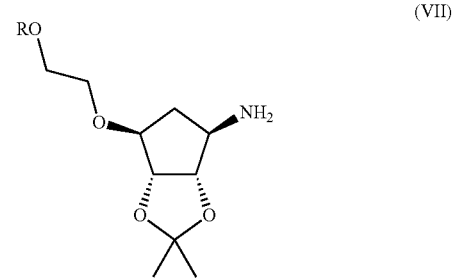

wherein R is as defined in the compound of Formula (VI).

Specifically, with addition of an appropriate base, the compound (VIII) in a solvent is reacted with the compound (VII) or an appropriate salt thereof at 0-100° C. to prepare the compound (VI). Said solvent is selected from the group consisting of methylbenzene, tetrahydrofuran, 2-methyltetrahydrofuran, dioxane, N,N-dimethyl formamide, N,N-dimethyl acetamide, acetonitrile, dichloromethane, trichloromethane, dichloroethane, dimethylbenzene, trimethylbenzene, methyl tertiary-butyl ether, cyclopentyl methyl ether and any combination thereof, preferably dioxane; said base is triethylamine, diisopropylethylamine (DIPEA), pyridine or 2,3,4-monoalkylated pyridine, preferably DIPEA; and the appropriate salt of said compound (VII) is L-tartrate, D-tartrate, L-dibenzoyl tartrate, D-dibenzoyl tartrate, L-mandelate, D-mandelate, oxalate, maleate or hippurate, preferably L-tartrate.

In Formula (VI), when R is hydrogen, namely when the compound of Formula (VI) is specifically the compound of Formula (VI'), besides the direct preparation method mentioned above, it is available to apply the method mentioned above to prepare the compound of Formula (VI) with R being such hydroxyl protecting group, then remove the hydroxyl protecting group to get the compound of Formula (VI'):

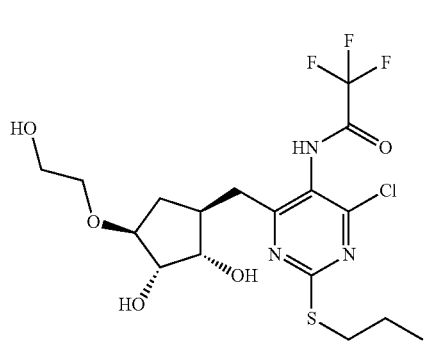

(VI')

The compound of Formula (VIII) can be prepared according to the following method: a compound of Formula (IX) is reacted with a trifluoroacetylation reagent to get the compound of Formula (VIII):

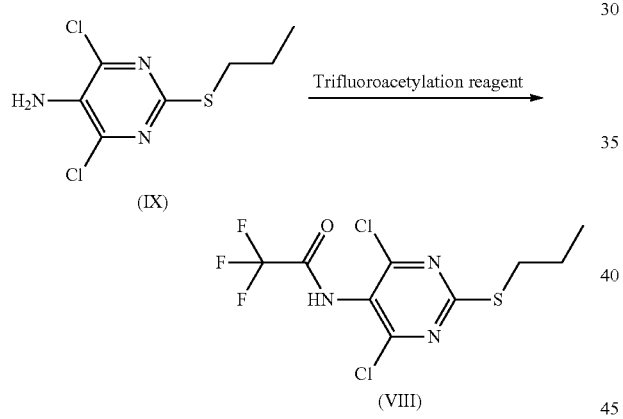

In the reaction mentioned above, said trifluoroacetylation reagent can be selected from the group consisting of trifluoroethyl acetate, trifluoroacetic anhydride, trifluoroacetoxy succinimide, (trifluoroacetyl)benzotriazole, pentafluorophenyl trifluoroacetate and 2-(trifluoroacetoxy)pyridine, preferably trifluoroacetic anhydride.

In another aspect, the present disclosure provides a compound of Formula (VIII):

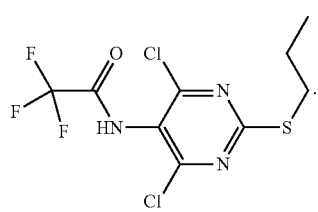

(VIII)

In yet another aspect, the present disclosure provides a Ticagrelor preparation method, comprising a step of preparing a compound of Formula (VI) as mentioned above, and a further step of preparing Ticagrelor from the compound of Formula (VI).

The method of further preparing Ticagrelor from the compound of Formula (VI) comprises the following steps of: at first, reacting the compound (VI) with a base in water or an appropriate solvent at 0-150° C. to prepare a compound (V), and then preparing Ticagrelor from the compound (V) according to a known method, for example, the method disclosed in Chinese Patent Application No. CN102149716A.

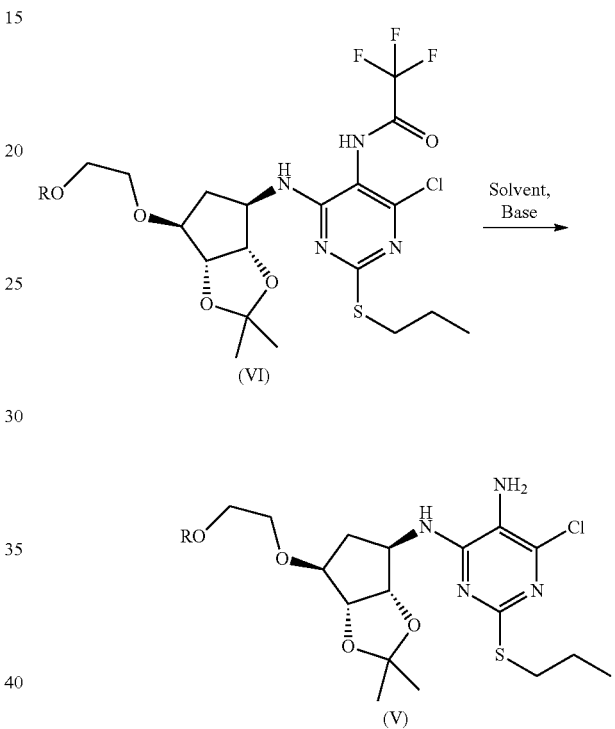

In a preferred embodiment, in the step of preparing the compound (V) from the compound (VI), said solvent is selected from the group consisting of water, $C_1$-$C_8$ lower fatty monohydric alcohol, $C_1$-$C_8$ lower fatty dihydric alcohol, methylbenzene, tetrahydrofuran, 2-methyltetrahydrofuran, dioxane, N,N-dimethyl formamide, N,N-dimethyl acetamide, acetonitrile, dichloromethane, trichloromethane, dichloroethane, dimethylbenzene, trimethylbenzene, methyl tertiary-butyl ether, cyclopentyl methyl ether and any combination thereof, preferably the mixture of ethanol and water; and said base is potassium carbonate, sodium carbonate, cesium carbonate, sodium bicarbonate, sodium phosphate, potassium phosphate, sodium hydroxide, potassium hydroxide, lithium hydroxide, calcium hydroxide or barium hydroxide, preferably potassium carbonate.

In a preferred embodiment of the present disclosure, the entire route of the Ticagrelor preparation method of the present disclosure is as shown below:

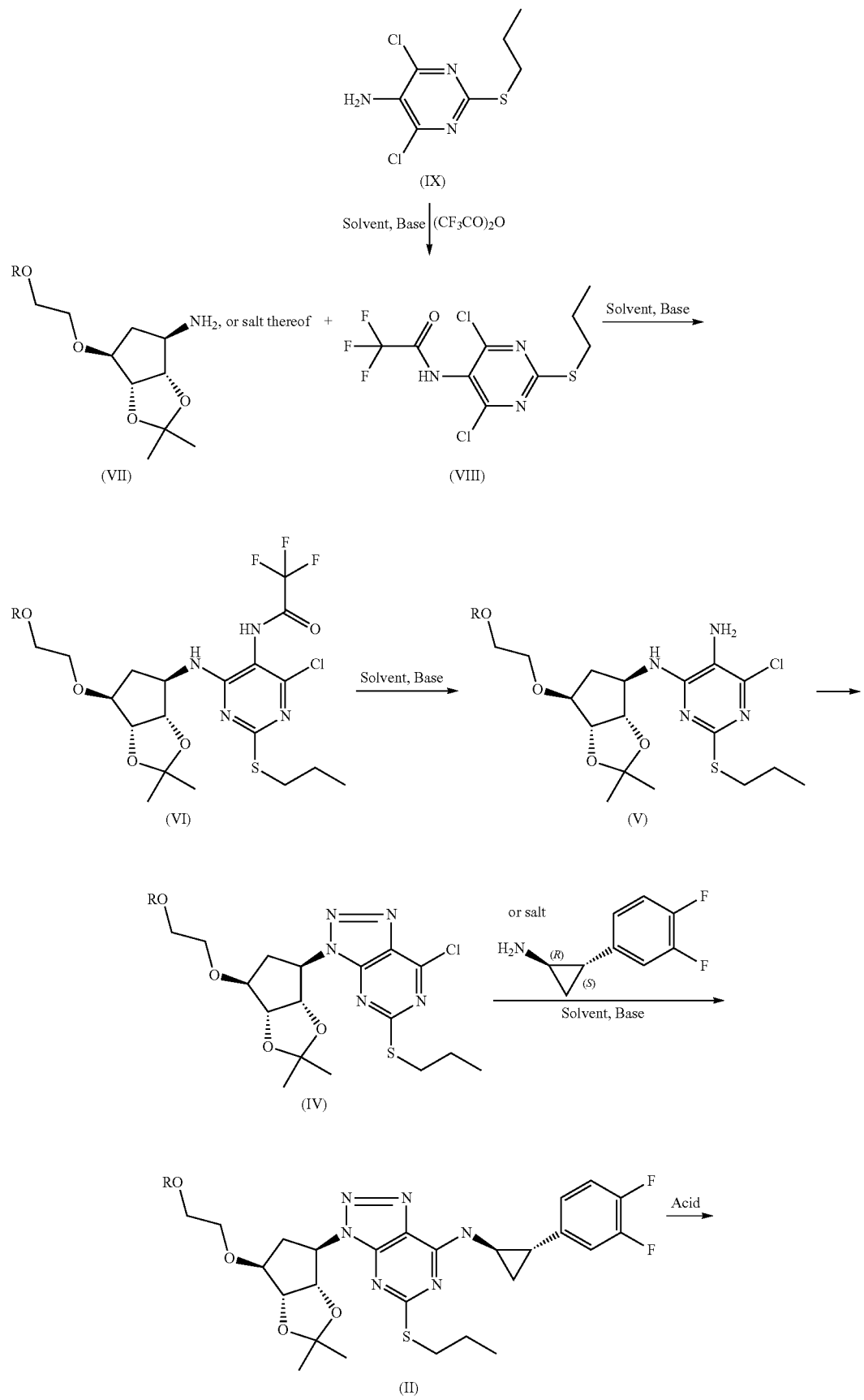

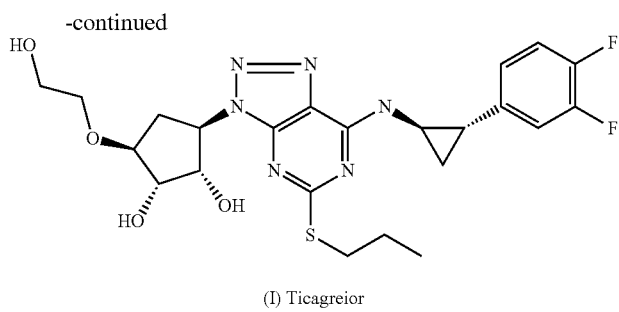

(I) Ticagreior wherein the reactions of preparing Ticagrelor from the compound (IV) through the compound (II) are detailed as below:

Preparation of Compound (IV)

In an appropriate acidic water, the compound (V) is reacted with an alkali metal nitrite at −10° C. to 30° C. to get the compound (IV).

Said acid is formic acid, acetic acid, diluted hydrochloric acid, diluted sulfuric acid, dilute phosphoric acid or any combination thereof, preferably acetic acid; and said alkali metal nitrite is sodium nitrite or potassium nitrite, preferably sodium nitrite.

Preparation of Compound (II)

With addition of an appropriate base, the compound (IV) in a solvent is reacted with (1R,2S)-2-(3,4-difluorophenyl)cyclopropylamine to prepare the compound (II).

Said solvent is selected from the group consisting of $C_1$-$C_8$ lower fatty monohydric alcohol, $C_1$-$C_8$ lower fatty dihydric alcohol, methylbenzene, tetrahydrofuran, 2-methyltetrahydrofuran, dioxane, N,N-dimethyl formamide, N,N-dimethyl acetamide, acetonitrile, dichloromethane, trichloromethane, dichloroethane, dimethylbenzene, trimethylbenzene, methyl tertiary-butyl ether, cyclopentyl methyl ether and any combination thereof, preferably methylbenzene; and said base is triethylamine, diisopropylethylamine, pyridine, 2,3,4-monoalkylated pyridine, potassium carbonate, sodium carbonate, cesium carbonate, sodium bicarbonate, sodium phosphate and potassium phosphate, preferably triethylamine.

Preparation of Compound (I) (Ticagrelor)

In water or a solvent, and with addition of an appropriate acidic deprotecting reagent, the protecting group of the compound (II) is removed to prepare Ticagrelor (I);

Said solvent is selected from the group consisting of methanol, ethanol, isopropanol, ethylene glycol, ethylene glycol monomethyl ether, ethylene glycol monobutyl ether, tetrahydrofuran, 2-methyltetrahydrofuran, dioxane, acetonitrile and any combination thereof; and the acidic deprotecting reagent is a certain concentration of hydrochloric acid or a certain concentration of trifluoroacetic acid, preferably hydrochloric acid, wherein R is a hydroxyl protecting group, preferably selected from the group consisting of triethylsilyl, triisopropylsilyl, t-butyldimethylsilyl, t-butyldiphenylsilyl, methoxymethyl, tetrahydropyranyl and tetrahydrofuranyl.

Besides the method mentioned above, the hydroxyl protecting group R can also be removed in advance, namely the hydroxyl protecting group is removed from the resulting compound (VI) to get the compound of Formula (VI'), which is then used to prepare Ticagrelor according to a similar method. Alternatively, in the compound (VII), R is directly hydrogen, namely the compound (VII') is used as starting material to prepare the compound (VI'), and then Ticagrelor is prepared according to a similar method of the route mentioned above. The specific subsequent preparation method of Ticagrelor is as described below:

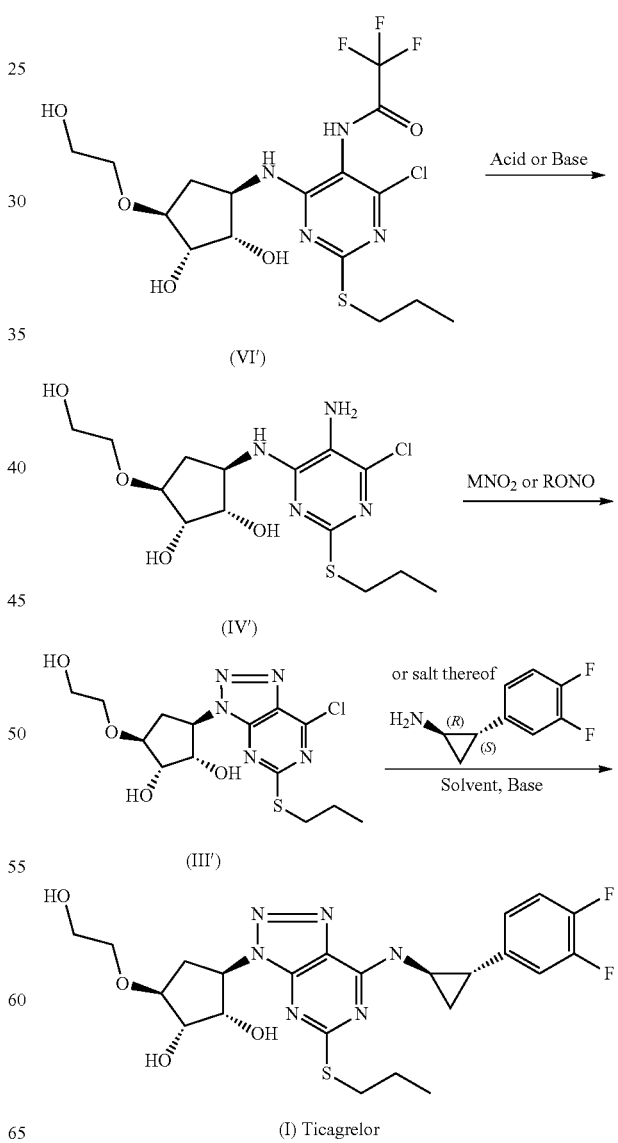

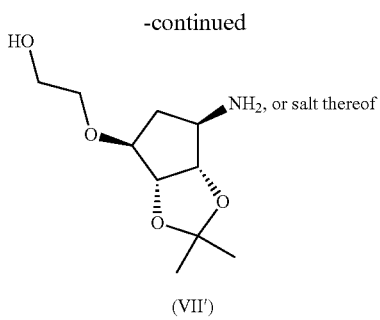

(VII')

wherein in the reaction of preparing the compound of Formula (IV') from the compound of Formula (VI'), said acid is selected from the group consisting of hydrochloric acid, methanesulfonic acid, trifluoromethanesulfonic acid, trifluoroacetic acid and sulfuric acid; or the base is selected from the group consisting of triethylamine, diisopropylethylamine, pyridine, 2,3,4-monoalkylated pyridine, N-methylmorpholine, anhydrous potassium carbonate, anhydrous sodium carbonate, anhydrous sodium bicarbonate, anhydrous sodium phosphate, anhydrous potassium phosphate, sodium hydroxide and lithium hydroxide.

The compound of said Formula (IV') is reacted with a base in a solvent; and said solvent is selected from the group consisting of methylbenzene, tetrahydrofuran, 2-methyltetrahydrofuran, dioxane, N,N-dimethyl formamide, N,N-dimethyl acetamide, dichloromethane, trichloromethane, dichloroethane, ethyl acetate, dimethylbenzene, trimethylbenzene, diethyl ether, isopropyl ether, methyl tertiary-butyl ether, cyclopentyl methyl ether and any combination thereof.

The compound of said Formula (IV') is reacted with an acid in a solvent; and said solvent is selected from a fatty alcohol with the number of carbon atoms less than 6, preferably methanol or ethanol.

The synthesis method for the intermediate (VI) provided by the present disclosure is simple. The trifluoroacetyl group is adopted to realize quantitative selective protection for aminopyrimidine, so that the reactivity of the chlorine atom of aminopyrimidine is greatly enhanced. As a result, the compound (VIII) is able to react with a chiral amino alcohol having the protected hydroxyl group (VII) or an appropriate salt thereof under a very mild condition, thereby avoiding the defect of long reaction times under high temperature as required in the existing methods. This method is suitable for industrial large-scale production, with the results of reducing the energy consumption, decreasing environmental pollution and reducing the discharge of waste effectively.

The "hydroxyl protecting groups" are known groups which are suitable for use to protect hydroxyl groups within the technical field. See the hydroxyl protecting groups disclosed in "Protective Groups in Organic Synthesis", 5$^{th}$ Ed., T. W. Greene & P. G. M. Wuts. As an example, preferably, said hydroxyl protecting group is a $(C_{1-10}$ alkyl or aryl$)_3$alkylsilyl group, for example, triethylsilyl, triisopropylsilyl, t-butyldimethylsilyl or t-butyldiphenylsilyl; a $C_{1-10}$ alkyl or substituted alkyl group, for example, methyl, t-butyl, allyl, benzyl, methoxymethyl, ethoxyethyl or 2-tetrahydropyranyl (THP); a $(C_{1-10}$ alkyl or aryl)acyl group, for example, formyl, acetyl or benzoyl; a $(C_{1-6}$ alkyl or $C_{6-10}$ aryl)sulfonyl group; or a $(C_{1-6}$ alkoxy or $C_{6-10}$ aryloxy)carbonyl group.

DETAILED DESCRIPTION OF THE INVENTION

The present disclosure is described in detail with reference to the following specific embodiments so that the technicians in the art will understand the present disclosure in a more comprehensive manner. The specific embodiments are used only to illustrate the technical solution of the present disclosure, but are not used to limit the scope of the present disclosure in any way.

EXAMPLE 1

Preparation of Compound (VIII)

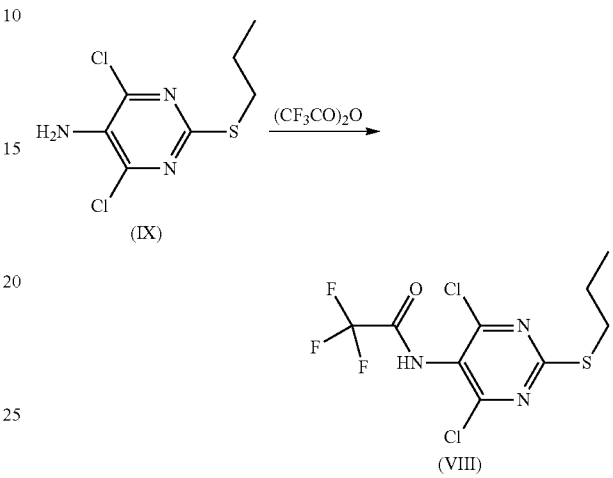

Method A: Compound (IX) (476.3 g, 2.0 mole) (IX was purchased from Shanghai Haoyuan Chemexpress Co., Ltd.) was dissolved in 4.0 L dichloromethane. Triethylamine (404 g, 4.0 mole) was added to the solution. The solution was cooled in ice water until the system internal temperature was below 10° C., and then trifluoroacetic anhydride (630 g, 3.0 mole) was slowly added dropwise to the solution. After trifluoroacetic anhydride was added completely, the solution was allowed to warm naturally to room temperature, and stirred for 1 hour. The reaction was monitored by HPLC. After the conversion of the raw material was complete, 2.0 L tap water was added to the reaction solution. The aqueous phase was extracted twice with 1.0 L dichloromethane, until there was no residual product in the aqueous phase. The organic phase was washed with 1.0 L saturated salt water, then dried for at least 3 h, filtered and concentrated to get 645 g compound (VIII) in 96% yield. The resulting product was directly used in the next step.

MS: m/z, (ESI): 335.2 [M+1]$^+$ $^1$H NMR (300 MHz, CDCl$_3$) δ 3.10 (t, 2H, J=4.8 Hz), 1.73 (m, 2H), 1.03 (t, 3H, J=4.8 Hz);

Preparation of Compound (VI-A)

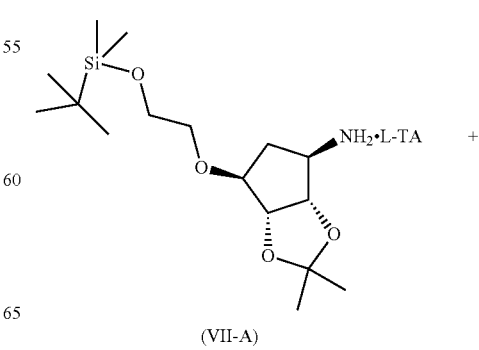

(VII-A)

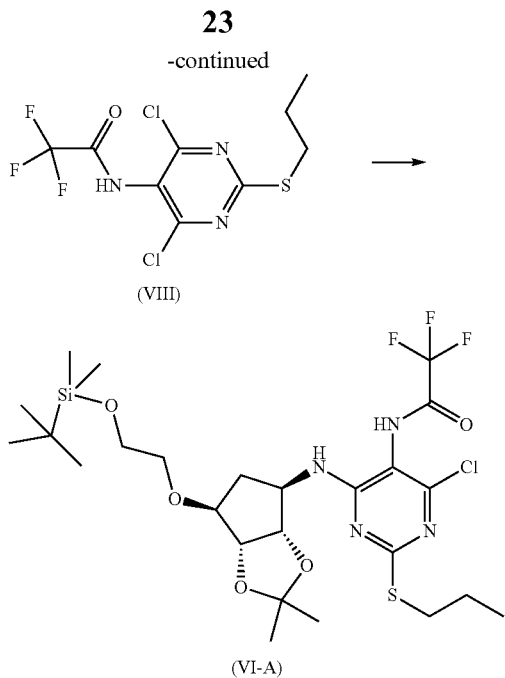

The L-tartrate of compound (VII-A) (662.3 g, 1.5 mole) (VII-A was purchased from Shanghai Haoyuan Chemexpress Co., Ltd.) and compound (VIII) (626.5 g, 1.75 mole) were dissolved in 12.5 L dioxane. Triethylamine (758 g, 7.5 mole) was added in batches. After triethylamine was completely added, the solution was heated to reflux for 12 h. The reaction was monitored by HPLC. After the reaction of compound (VII) was complete, most of the solvent was removed through concentration. Then, 5 L deionized water was added to the reaction system under stirring to precipitate a pale yellow solid, and then it was filtered and dried to get 802 g compound (VI-A) in 85% yield.

MS: m/z, (ESI): 629.2 [M+1]$^+$ $^1$H NMR (300 MHz, CDCl$_3$) δ 7.10 (s, 1H), 6.19 (d, 1H, J=6.0 Hz), 4.58 (t, 2H, J=5.1 Hz), 4.48 (d, 1H, J=3.9 Hz), 3.97 (d, 1H, J=3.0 Hz), 3.75 (d, 2H, J=3.0 Hz), 3.61-3.66 (m, 1H), 3.53-3.57 (m, 1H), 3.10-3.18 (m, 1H), 2.98-3.05 (m, 1H), 2.23-2.29 (m, 1H), 1.73-1.80 (m, 2H), 1.42 (s, 3H), 1.26 (s, 3H), 1.02-1.05 (t, 3H), 0.873 (s, 9H), 0.05 (s, 6H);

Preparation of Compound (V-A)

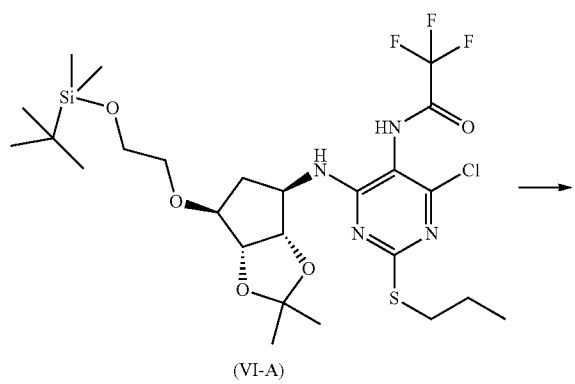

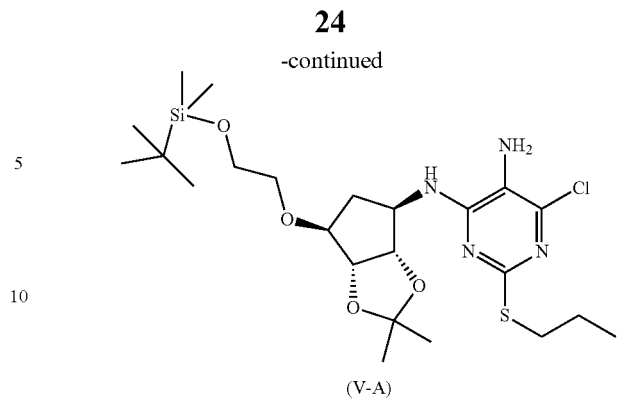

Compound (VI-A) (500 g, 0.8 mole) was dissolved in 5.0 L ethanol. Solid potassium carbonate (220 g, 1.6 mole) was added to the solution in one batch. The solution was heated to reflux for 24 h. The reaction was monitored by HPLC. After the reaction was complete, ethanol was removed through concentration, and the residue was poured into 5 L deionized water. A large amount of pale yellow solid was precipitated from the system, and then it was filtered and dried under vacuum to get 405 g compound (V-A) in 95% yield.

Preparation of Compound (IV-A)

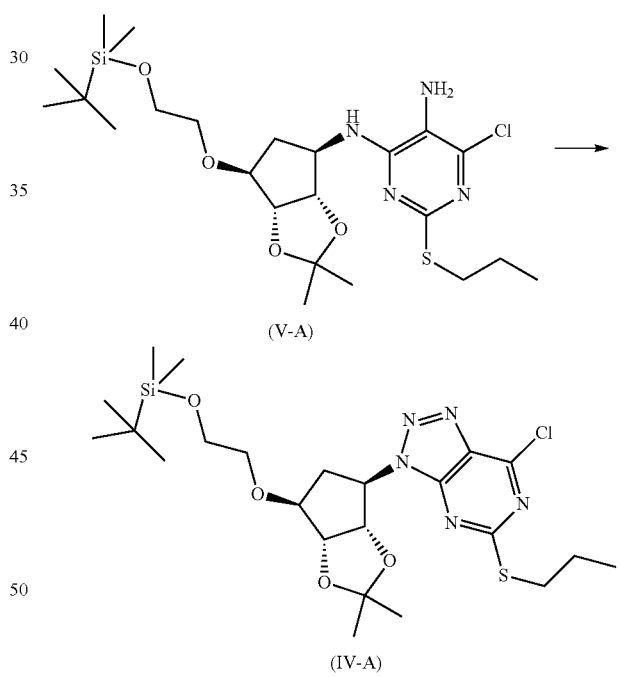

Compound (V-A) (400 g, 0.75 mole) was dissolved in 3.5 L glacial acetic acid. Then, 600 mL deionized water was added to the solution. The solution was cooled in an ice-salt bath until the system internal temperature was below 10° C. Then, 400 mL of an aqueous solution of sodium nitrite (77.6 g, 1.13 mole) was slowly added dropwise to the reaction mixture. After sodium nitrite was added completely, the reaction mixture was allowed to warm naturally to room temperature. The reaction was monitored by HPLC. After the reaction was complete, solid potassium carbonate was added until the pH value of the solution was neutral. The reaction solution was extracted twice with 3 L ethyl acetate. The organic phase was washed with saturated salt water, then dried and concentrated to get 367 g compound (IV-A) in 90% yield.

Preparation of Compound (II-A)

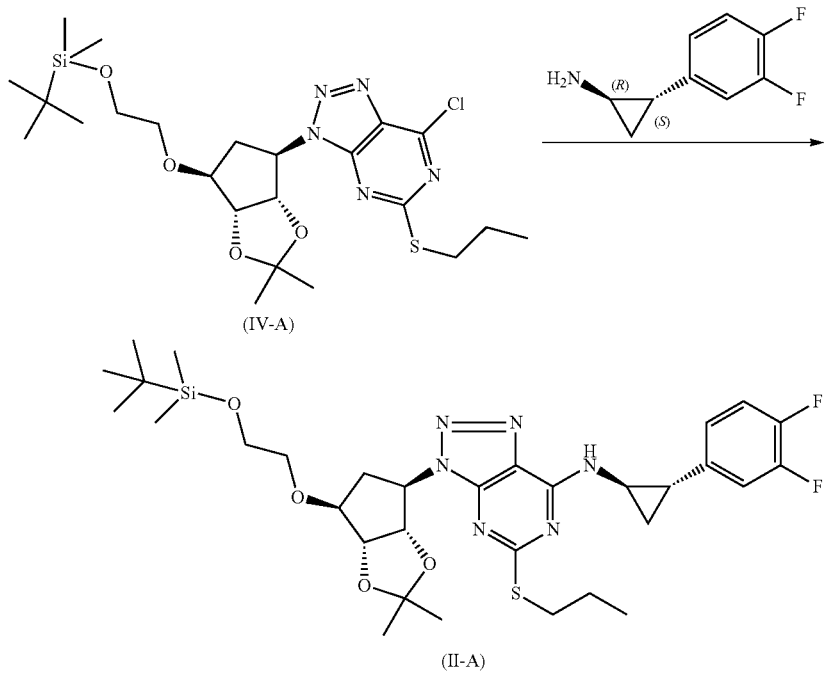

Compound (IV-A) (350 g, 0.64 mole) and the oxalate of (1R,2S)-2-(3,4-difluorophenyl)cyclopropylamine (168.5 g, 0.65 mole) were dissolved in 2.0 L methylbenzene. Potassium carbonate (270 g, 1.95 mole) was added to the solution. The solution was stirred at room temperature for 24 h. The reaction was monitored by HPLC. After the reaction was complete, 500 mL deionized water was added to the system. The organic phase was washed with saturated salt water, then dried and concentrated to get 367 g compound (II-A) in 85% yield.

Preparation of Compound (I)

Compound (II-A) (100 g, 0.15 mole) was dissolved in 3.0 L methanol. Then, 1.0 L 3M hydrochloric acid solution was added to the reaction solution. The reaction solution was heated up to 30° C. for 24 h. The reaction was monitored by HPLC. After the reaction was complete, most of the solvent was removed through concentration. Then, 2.0 L ethyl acetate was added to the residual solution. The aqueous phase was separated, and then extracted with 1.0 L ethyl acetate. The organic phase was combined, and washed with saturated salt water. The washed organic phase was dried and concentrated to get 70.0 g crude product of compound (I) in 90% yield. The crude product was dissolved in 300 mL ethyl acetate, and heated up to 50° C. After the crude product was completely dissolved, 500 mL n-heptane was added to the solution. The solution was cooled down slowly to 20° C., and then filtered to get 60 g white solid purified product of compound (I) with a purity up to 99% and in 85% yield.

MS: m/z, (ESI): 523.2 [M+1]

$^1$H NMR (400 MHz, DMSO-$d_6$) δ 7.20-7.35 (m, 2H), 7.00-7.10 (m, 1H), 5.10 (d, 1H), 5.03 (d, 1H), 4.95 (dd, 1H), 4.50-4.60 (m, 2H), 3.90-4.00 (m, 1H), 3.75-3.85 (m, 1H), 3.45-3.55 (m, 4H), 3.10-3.20 (m, 1H), 2.75-3.00 (m, 2H), 2.55-2.70 (m, 1H), 2.10-2.20 (m, 1H), 1.95-2.05 (m, 1H), 1.65-1.75 (m, 0.5H), 1.30-1.60 (m, 4H), 1.20-1.30 (m, 0.5H), 0.81 (t, 3H).

EXAMPLE 2

Preparation of Compound (VIII)

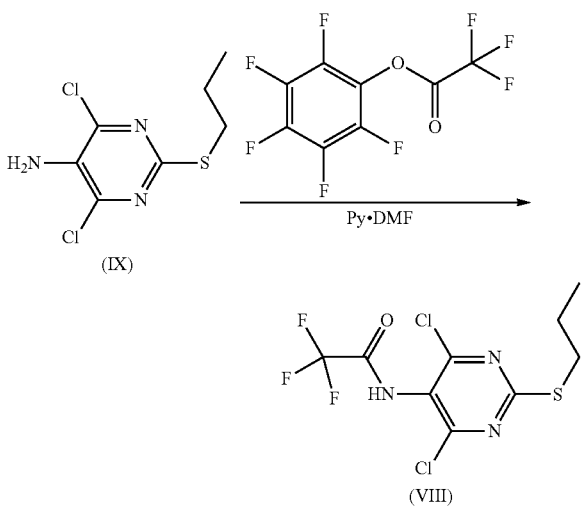

Method B: Compound (IX) (150 g, 0.6 mole) (IX was purchased from Shanghai Haoyuan Chemexpress Co., Ltd.) was dissolved in 1.0 L N,N-dimethyl formamide (DMF). Pyridine (69.3 g, 1.0 mole) was added to the solution. The solution was cooled in ice water until the system internal temperature was below 10° C. Pentafluorophenyl trifluoroacetate (184.5 g, 0.66 mole) was slowly added dropwise to the solution. After pentafluorophenyl trifluoroacetate was added completely, the solution was allowed to warm naturally to room temperature, and was stirred for 5 h. The reaction was monitored by HPLC. After the conversion of the raw material was complete, 2.0 L tap water was added to the reaction solution. The reaction solution was extracted twice with 1.0 L methyl tertiary-butyl ether. The organic phase was washed with 0.5 L saturated salt water, then dried for not less than 3 h, filtered and concentrated to get 186.2 g compound (VIII) in 93% yield. The resulting product was directly used in the next step.

Preparation of Compound (VI-B)

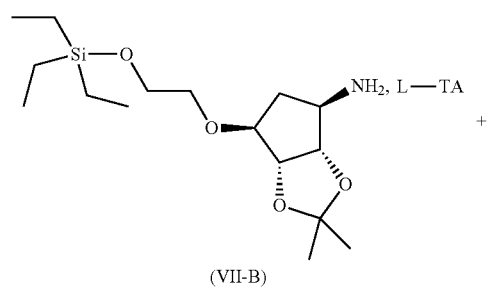

(VII-B)

+

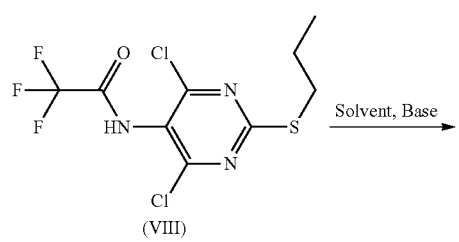

(VIII)

Solvent, Base →

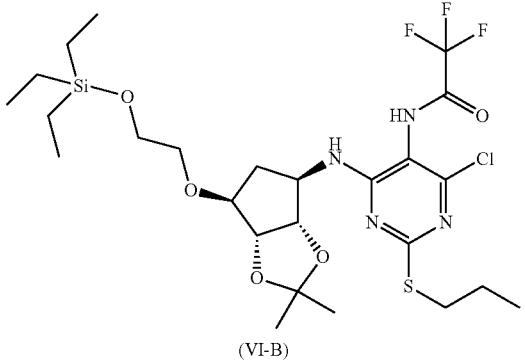

(VI-B)

The L-tartrate of compound (VII-B) (200 g, 0.4 mole) (VII-B was purchased from Shanghai Haoyuan Chemexpress Co., Ltd.) and compound (VIII) (147 g, 0.44 mole) were dissolved in 3.5 L dioxane. Triethylamine (155.4 g, 1.4 mole) was added in batches. After triethylamine was completely added, the solution was heated up to 80° C. for 3 h. The reaction was monitored by HPLC. After the reaction of compound (VII) was complete, most of the solvent was removed through concentration. 1 L deionized water was added to the reaction system under stirring to precipitate a pale yellow solid, and then it was filtered and dried to get 196.2 g compound (VI-B) in 78% yield.

Preparation of Compound (V-B)

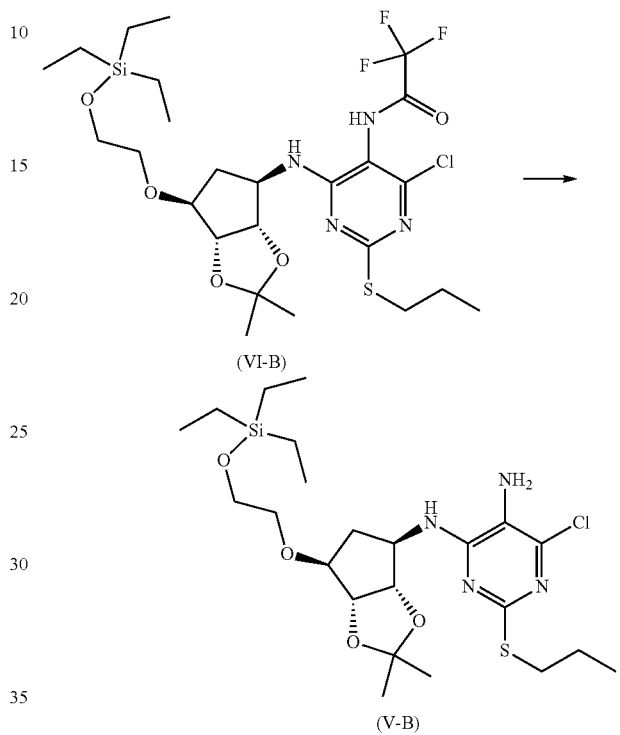

(VI-B)

(V-B)

Compound (VI-B) (100 g, 0.16 mole) was dissolved in 1.0 L methanol. Solid potassium carbonate (110 g, 0.8 mole) was added to the solution in one batch. The solution was heated to reflux for 24 h. The reaction was monitored by HPLC. After the reaction was complete, methanol was removed through concentration, and the residue was poured into 1 L deionized water. A large amount of pale yellow solid was precipitated from the system, and then it was filtered and dried under vacuum to get 72.4 g compound (V-B) in 85% yield.

Preparation of Compound (IV-B)

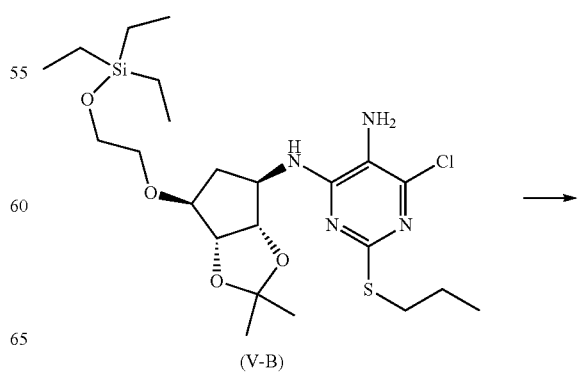

(V-B)

-continued

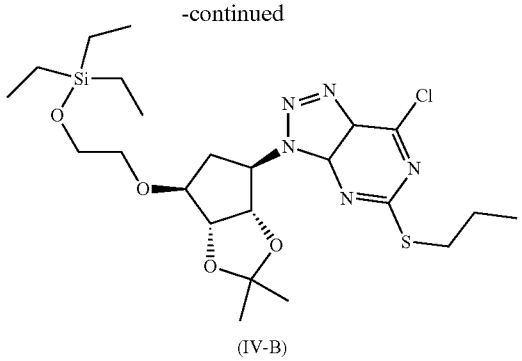

(IV-B)

Compound (V-B) (50 g, 0.15 mole) was dissolved in 1.25 L glacial acetic acid. Then, 600 mL deionized water was added to the solution. The solution was cooled in an ice-salt bath until the system internal temperature was below 10° C. Then, 400 mL of an aqueous solution of sodium nitrite (13.8 g, 0.2 mole) was slowly added dropwise to the reaction mixture. After sodium nitrite was added completely, the reaction mixture was allowed to warm naturally to room temperature. The reaction was monitored by HPLC. After the reaction was complete, solid potassium carbonate was added until the pH value of the solution was neutral. The reaction solution was extracted twice with 1.5 L ethyl acetate. The organic phase was washed with saturated salt water, then dried and concentrated to get 63.6 g compound (IV-B) in 78% yield.

Preparation of Compound (II-B)

Compound (IV-B) (54 g, 0.1 mole) and the hydrochloride of (1R,2S)-2-(3,4-difluorophenyl)cyclopropylamine (21 g, 0.105 mole) was dissolved in 1.0 L acetonitrile Anhydrous sodium bicarbonate (32 g, 0.3 mole) was added to the solution, which was then stirred at room temperature for 16 h. The reaction was monitored by HPLC. After the reaction was complete, 500 mL deionized water was added to the system, and the system was extracted with 500 mL ethyl acetate. The organic phase was washed with saturated salt water, then dried and concentrated to get 57.5 g compound (II-B) in 85% yield.

MS: m/z, (ESI): 677.91 [M+1]

EXAMPLE 3

Preparation of Compound (V)

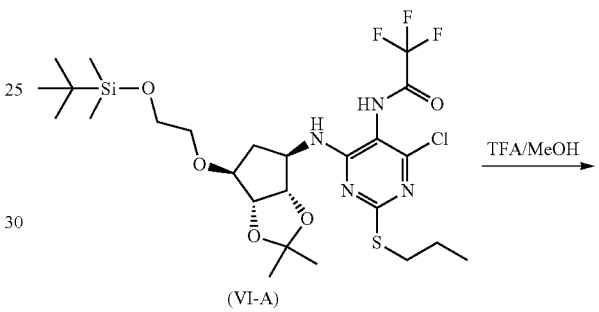

(VI-A)

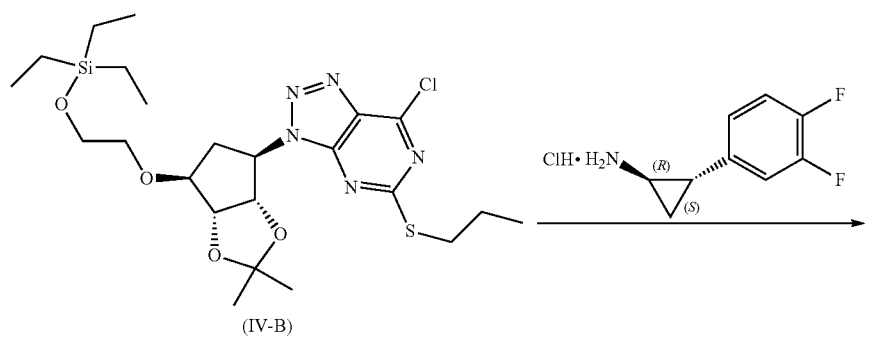

(IV-B)

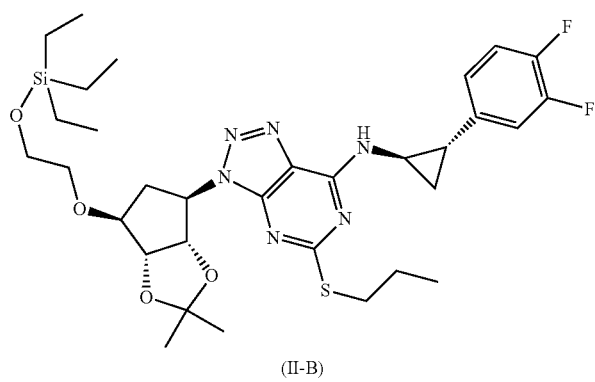

(II-B)

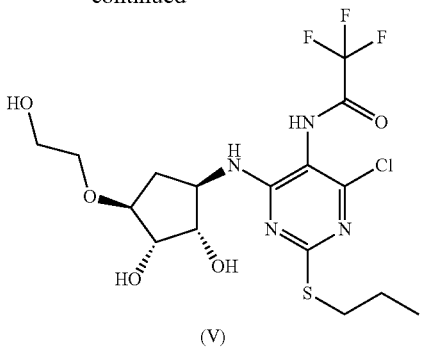

(V)

Compound (VI-A) (100 g, 0.16 mole) was dissolved in 1.0 L anhydrous methanol. Trifluoroacetic acid was added dropwise to the solution and the temperature was controlled below 50° C. After trifluoroacetic acid was added completely, the solution was stirred at room temperature for 24 h. The reaction was monitored by HPLC. After the reaction was complete, most of the solvent was removed through concentration, and 1 kg deionized water was added to the residual solution to precipitate a large amount of yellow solid, which was then filtered and dried under vacuum to get 73 g compound (V) in 96% yield.

MS: m/z, (ESI): 475.91 [M+1]

Preparation of Compound (IV)

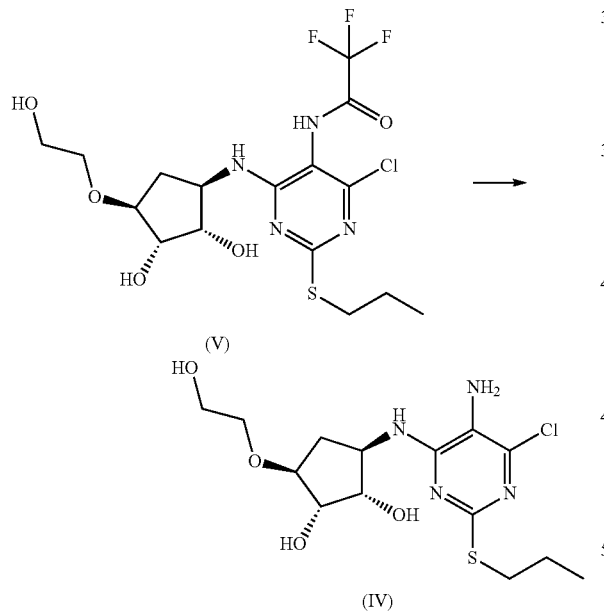

Compound (V) (50 g, 0.11 mole) was dissolved in 500 mL ethanol. Solid potassium carbonate (53 g, 0.385 mole) was added to the solution in one batch. The solution was heated to reflux for 24 h. The reaction was monitored by HPLC. After the reaction was complete, ethanol was removed through concentration, and the residue was poured into 1.0 L deionized water. Pale yellow solid was precipitated from the system, and then it was filtered and dried under vacuum to get 37 g compound (IV) in 90% yield.

MS: m/z, (ESI): 379.87 [M+1]$^+$

Preparation of Compound (III)

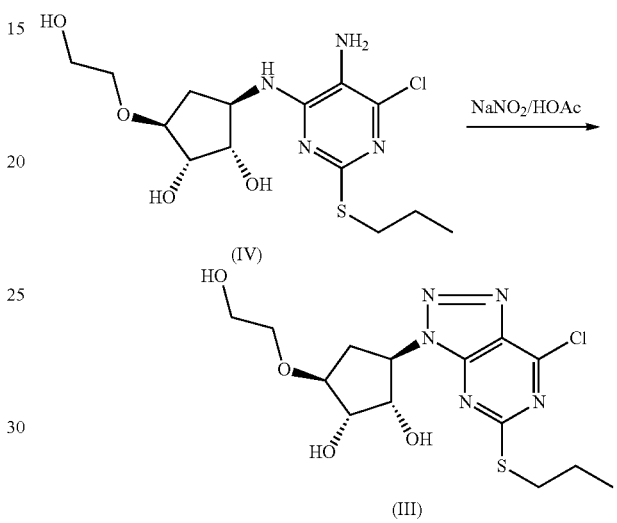

Compound (IV) (50 g, 0.12 mole) was dissolved in 1.5 L glacial acetic acid. 600 mL deionized water was added to the solution. The solution was cooled in an ice-salt bath until a system internal temperature was below 10° C. Then, 100 mL of an aqueous solution of sodium nitrite (12.4 g, 0.18 mole) was slowly added dropwise to the reaction mixture. After sodium nitrite was added completely, the reaction mixture was allowed to warm naturally to room temperature. The reaction was monitored by HPLC. After the reaction was complete, solid potassium carbonate was added until the pH value of the solution was neutral. The reaction solution was extracted twice with 3 L ethyl acetate. The organic phase was washed with saturated salt water, then dried and concentrated to get 44.5 g compound (III) in 95% yield.

MS: m/z, (ESI): 390.87 [M+1]

Preparation of Compound (I)

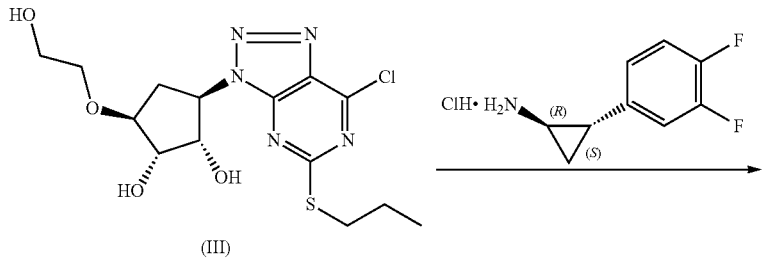

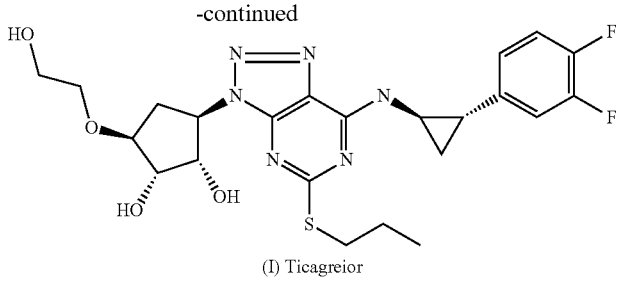

(I) Ticagrelor

Compound (III) (40 g, 0.10 mole) and the hydrochloride of (1R,2S)-2-(3,4-difluorophenyl)cyclopropylamine (30.8 g, 0.15 mole) were dissolved in 1.0 L dry tetrahydrofuran. Potassium carbonate (42 g, 0.3 mole) was added to the solution. The solution was stirred at room temperature for 24 h. The reaction was monitored by HPLC. After the reaction was complete, 500 mL deionized water was added to the system. The organic phase was washed with saturated salt water, then dried and concentrated to get 46.5 g compound (I) in 89% yield. The crude product was dissolved in 150 mL ethyl acetate, and heated up to 50° C. After the product was completely dissolved, 300 mL n-heptane was added to the solution. The solution was cooled down slowly to 20° C., and then filtered to get 60 g purified white solid compound (I), namely Ticagrelor, with a purity up to 99% and in 95% yield.

MS: m/z, (ESI): 523.2 [M+1]

$^1$H NMR (400 MHz, DMSO-$d_6$) δ 7.20-7.35 (m, 2H), 7.00-7.10 (m, 1H), 5.10 (d, 1H), 5.03 (d, 1H), 4.95 (dd, 1H), 4.50-4.60 (m, 2H), 3.90-4.00 (m, 1H), 3.75-3.85 (m, 1H), 3.45-3.55 (m, 4H), 3.10-3.20 (m, 1H), 2.75-3.00 (m, 2H), 2.55-2.70 (m, 1H), 2.10-2.20 (m, 1H), 1.95-2.05 (m, 1H), 1.65-1.75 (m, 0.5H), 1.30-1.60 (m, 4H), 1.20-1.30 (m, 0.5H), 0.81 (t, 3H).

Since the present disclosure has been described based on the specific embodiments thereof, some modifications and equivalent variations that are apparent to those skilled in the art are also within the scope of the present disclosure.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A compound of Formula (VI):

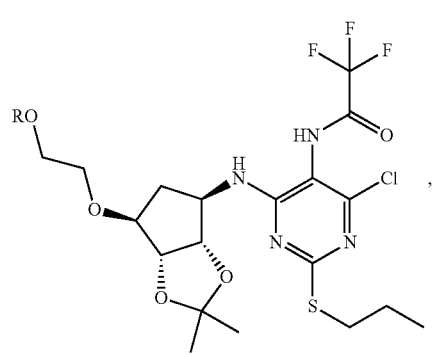

wherein R is hydrogen or a hydroxyl protecting group.

2. A preparation method for the compound of Formula (VI) according to claim 1, comprising a step of reacting a compound of Formula (VIII) with a compound of Formula (VII) or a salt thereof:

(VIII)

(VII)

3. The preparation method according to claim 2, wherein the method further comprises a step of removing the hydroxyl protecting group from the compound of Formula (VI) in the presence of an acid to produce a compound of Formula (VI'):

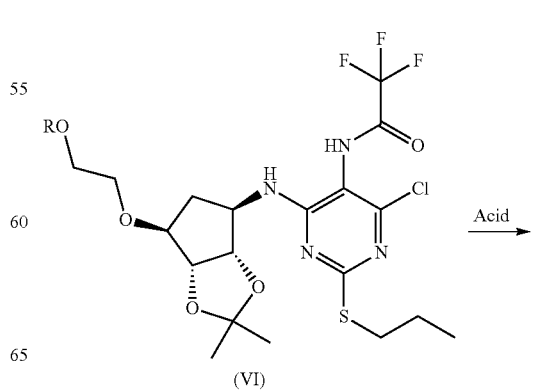

-continued

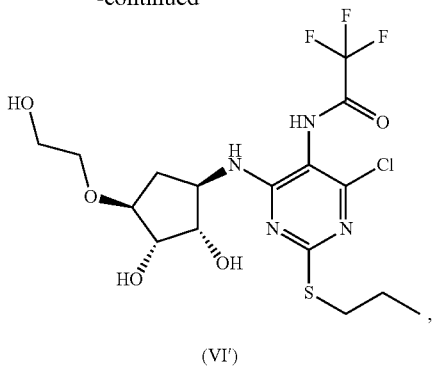

(VI')

wherein R is a hydroxyl protecting group.

4. The preparation method according to claim 2, wherein the reaction is carried out in the presence of a base.

5. The preparation method according to claim 2, wherein a reaction temperature ranges from 0° C. to 100° C.

6. The preparation method according to claim 2, wherein the reaction is carried out in a solvent; and the solvent is selected from the group consisting of methylbenzene, tetrahydrofuran, 2-methyltetrahydrofuran, dioxane, N,N-dimethyl formamide, N,N-dimethyl acetamide, acetonitrile, dichloromethane, trichloromethane, dichloroethane, dimethylbenzene, trimethylbenzene, methyl tertiary-butyl ether, cyclopentyl methyl ether, and any combination thereof.

7. The preparation method according to claim 2, wherein the method further comprises a step of reacting a compound of Formula (IX) with a trifluoroacetylation reagent to produce the compound of Formula (VIII):

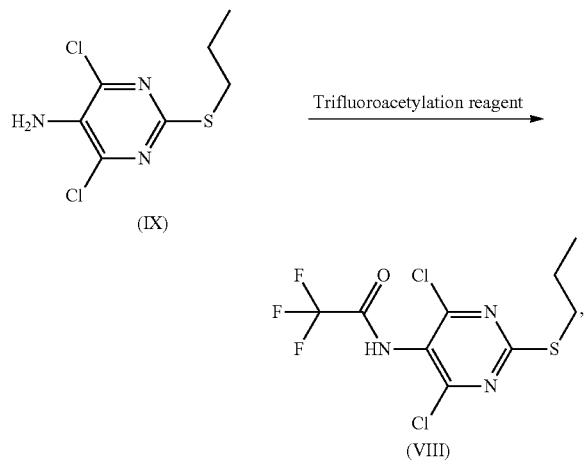

wherein said trifluoroacetylation reagent is selected from the group consisting of trifluoroethyl acetate, trifluoroacetic anhydride, trifluoroacetoxy succinimide, (trifluoroacetyl)benzotriazole, pentafluorophenyl trifluoroacetate, and 2-(trifluoroacetoxy)pyridine.

8. The preparation method according to claim 7, wherein the reaction is carried out in the presence of a base; and the base is selected from the group consisting of triethylamine, diisopropylethylamine, pyridine, 2,3,4-monoalkylated pyridine, anhydrous potassium carbonate, anhydrous sodium carbonate, anhydrous sodium bicarbonate, anhydrous sodium phosphate and anhydrous potassium phosphate.

9. The preparation method according to claim 7, wherein the reaction is carried out in a solvent; and the solvent is selected from the group consisting of methylbenzene, tetrahydrofuran, 2-methyltetrahydrofuran, dioxane, N,N-dimethyl formamide, N,N-dimethyl acetamide, dichloromethane, trichloromethane, dichloroethane, ethyl acetate, dimethylbenzene, trimethylbenzene, diethyl ether, isopropyl ether, methyl tertiary-butyl ether, cyclopentyl methyl ether, and any combination thereof.

10. A compound of Formula (VIII):

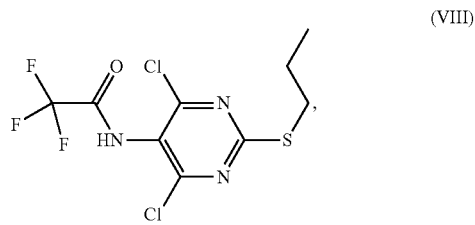 [SMILES: CCCSc1nc(Cl)c(NC(=O)C(F)(F)F)c(Cl)n1]

11. A preparation method for a compound of formula (I):

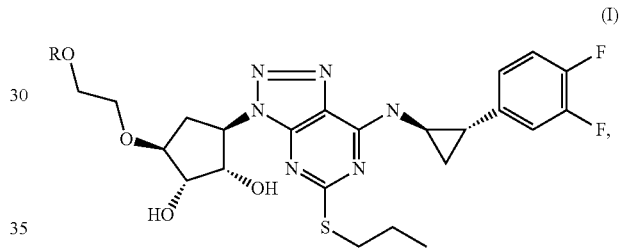

wherein the method comprises a step of preparing the compound of Formula (VI) according to claim 2 and a step of preparing the compound of formula (I) from the compound of Formula (VI); wherein in Formula (VI), R is a hydroxyl protecting group.

12. The preparation method according to claim 11, wherein the step of preparing the compound of Formula (I) from the compound of Formula (VI) is a multi-step reaction, comprising a step of reacting the compound of Formula (VI) with a base to produce a compound of Formula (V) and a subsequent step of preparing the compound of Formula (I) from the compound of Formula (V):

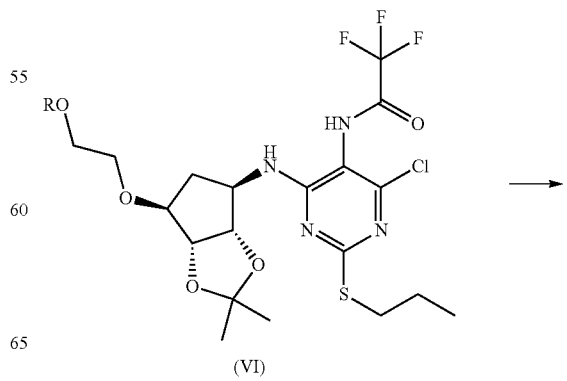

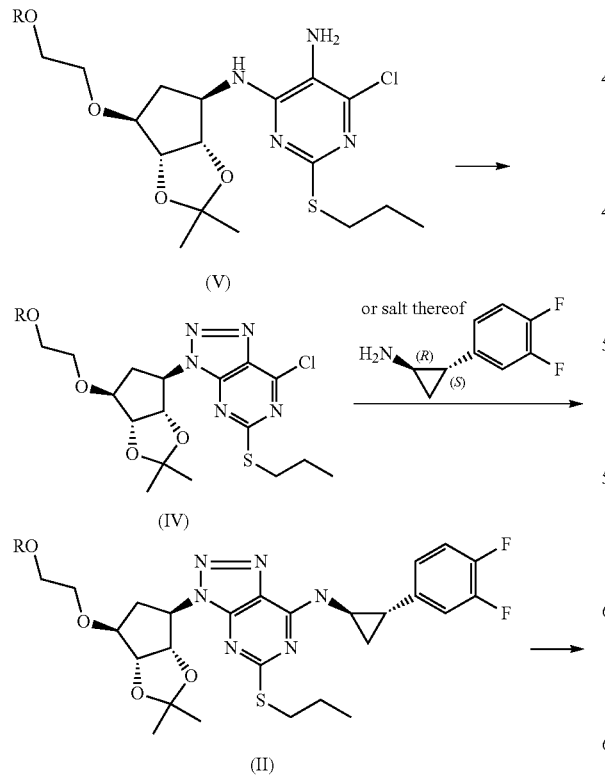

(V)

13. The preparation method according to claim 12, wherein the base is selected from the group consisting of triethylamine, diisopropylethylamine, pyridine, 2,3,4-monoalkylated pyridine, anhydrous potassium carbonate, anhydrous sodium carbonate, anhydrous sodium bicarbonate, anhydrous sodium phosphate, and anhydrous potassium phosphate.

14. The preparation method according to claim 12, wherein the compound of Formula (VI) is reacted with the base in a solvent; and the solvent is selected from the group consisting of methylbenzene, tetrahydrofuran, 2-methyltetrahydrofuran, dioxane, N,N-dimethyl formamide, N,N-dimethyl acetamide, dichloromethane, trichloromethane, dichloroethane, ethyl acetate, dimethylbenzene, trimethylbenzene, diethyl ether, isopropyl ether, methyl tertiary-butyl ether, cyclopentyl methyl ether, and any combination thereof.

15. The preparation method according to claim 12, wherein the step of further preparing the compound of Formula (I) from the compound of Formula (V) comprises the following steps:

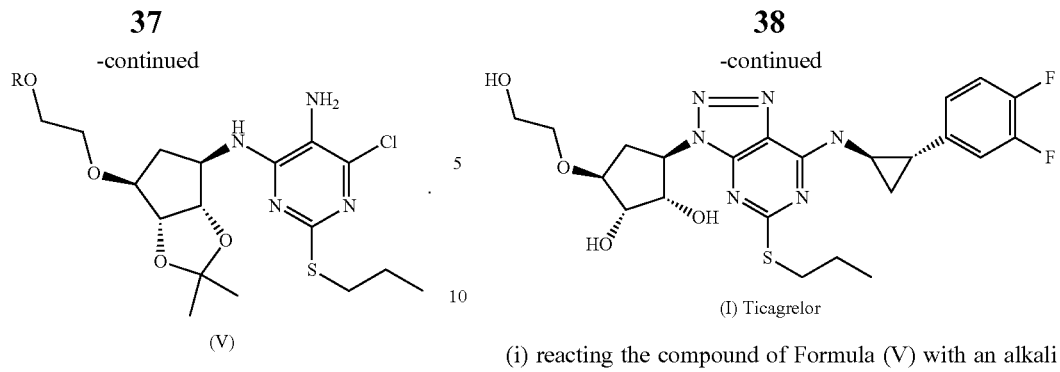

(I) Ticagrelor (i) reacting the compound of Formula (V) with an alkali metal nitrite to produce a compound of Formula (IV);
(ii) reacting the compound of Formula (IV) with a (1R,2S)-2-(3,4-difluorophenyl)cyclopropylamine or a salt thereof to produce a compound of Formula (II); and
(iii) deprotecting the compound of Formula (II) to prepare the compound of Formula (I).

16. A preparation method for a compound of Formula (I):

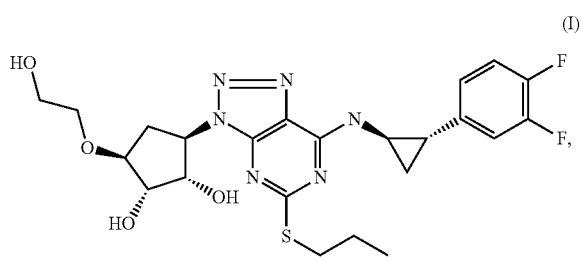 [SMILES: CCCSc1nc(N[C@@H]2C[C@H]2c2ccc(F)c(F)c2)c2nnn([C@@H]3C[C@H](OCCO)[C@@H](O)[C@H]3O)c2n1]

(I)

wherein the method comprises a step of preparing the compound of Formula (VI') according to claim 3, and a step of preparing the compound of Formula (I) from the compound of Formula (VI').

17. The preparation method according to claim 16, wherein the step of preparing the compound of Formula (I) from the compound of Formula (VI') is a multi-step reaction, comprising a step of reacting the compound of Formula (VI') with a strong acid or a base to produce the compound of Formula (IV'), and a further step of preparing the compound of Formula (I) from the compound of Formula (IV'):

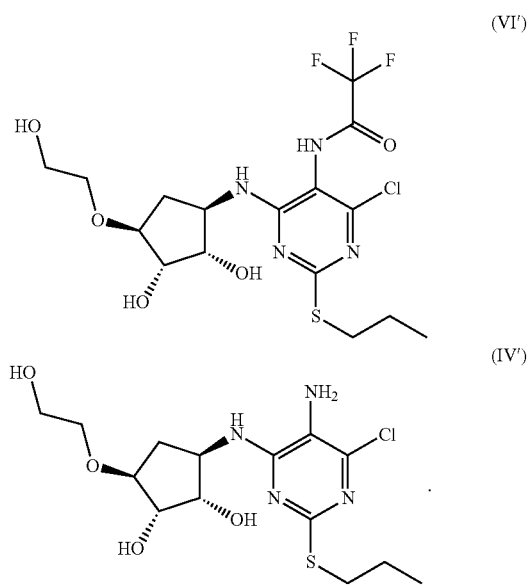

18. The preparation method according to claim 17, wherein the strong acid is selected from the group consisting of hydrochloric acid, methanesulfonic acid, trifluoromethanesulfonic acid, trifluoroacetic acid and sulfuric acid; and the base is selected from the group consisting of triethylamine, diisopropylethylamine, pyridine, 2,3,4-monoalkylated pyridine, N-methylmorpholine, anhydrous potassium carbonate, anhydrous sodium carbonate, anhydrous sodium bicarbonate, anhydrous sodium phosphate, anhydrous potassium phosphate, sodium hydroxide, and lithium hydroxide.

19. The preparation method according to claim 17, wherein the compound of Formula (IV') is reacted with the base in a solvent; and the solvent is selected from the group consisting of methylbenzene, tetrahydrofuran, 2-methyltetrahydrofuran, dioxane, N,N-dimethyl formamide, N,N-dimethyl acetamide, dichloromethane, trichloromethane, dichloroethane, ethyl acetate, dimethylbenzene, trimethylbenzene, diethyl ether, isopropyl ether, methyl tertiary-butyl ether, cyclopentyl methyl ether, and any combination thereof.

20. The preparation method according to claim 17, wherein the compound of Formula (IV') reacts with the strong acid in a solvent; and the solvent is selected from the group consisting of fatty alcohols having less than 6 carbon atoms.

21. The preparation method according to claim 17, wherein the further step of preparing the compound of Formula (I) from the compound of Formula (IV') comprises the following steps:

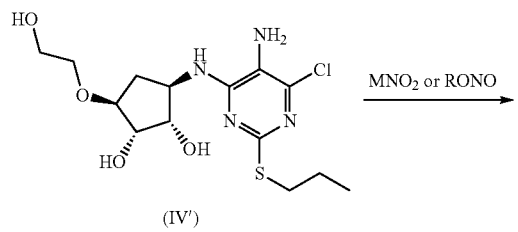

(IV')

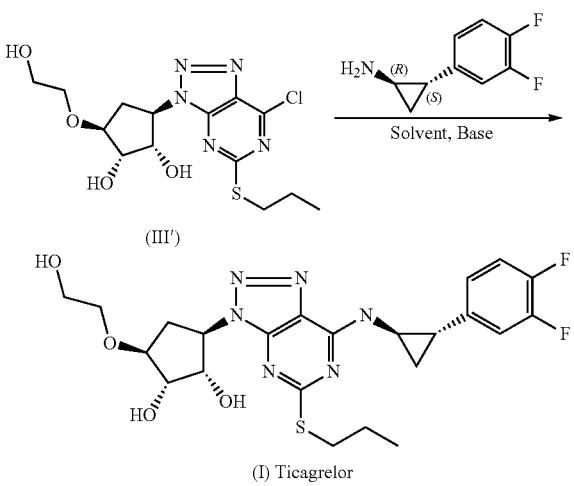

(i) reacting the compound of Formula (IV') with an alkali metal nitrite to produce a compound of Formula (III'); and (ii) reacting the compound of Formula (III') with (1R,2S)-2-(3,4-difluorophenyl)cyclopropylamine or a salt thereof to produce the compound of Formula (I).

22. The compound of Formula (VI) according to claim 1, wherein the hydroxyl protecting group is selected from the group consisting of trimethylsilyl, triethylsilyl, triisopropylsilyl, t-butyldimethylsilyl, t-butyldiphenylsilyl, methoxymethyl, tetrahydropyranyl, and tetrahydrofuranyl.

23. The preparation method according to claim 2, wherein the salt of the compound of Formula (VII) is L-tartrate, D-tartrate, L-dibenzoyl tartrate, D-dibenzoyl tartrate, L-mandelate, D-mandelate, oxalate, maleate, or hippurate.

24. The method of claim 4, wherein the base is triethylamine, diisopropylethylamine, pyridine, or 2,3,4-monoalkylated pyridine.

* * * * *